United States Patent
Dvir et al.

(10) Patent No.: US 11,213,609 B2
(45) Date of Patent: Jan. 4, 2022

(54) PARTICLES COMPRISING DECELLULARIZED OMENTUM

(71) Applicant: Ramot at Tel-Aviv University Ltd., Tel Aviv (IL)

(72) Inventors: Tal Dvir, LeHavim (IL); Assaf Shapira, Moshav Talmei Elazar (IL); Michal Shevach, Tel-Aviv (IL); Idan Gal, Rishon-LeZion (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 16/061,675

(22) PCT Filed: Dec. 15, 2016

(86) PCT No.: PCT/IL2016/051344
§ 371 (c)(1),
(2) Date: Jun. 13, 2018

(87) PCT Pub. No.: WO2017/103930
PCT Pub. Date: Jun. 22, 2017

(65) Prior Publication Data
US 2018/0361023 A1    Dec. 20, 2018

Related U.S. Application Data

(60) Provisional application No. 62/268,046, filed on Dec. 16, 2015.

(51) Int. Cl.
| | | |
|---|---|---|
| A61L 27/36 | (2006.01) | |
| A61K 35/35 | (2015.01) | |
| A61L 27/38 | (2006.01) | |
| A61L 27/54 | (2006.01) | |
| B82Y 5/00 | (2011.01) | |

(52) U.S. Cl.
CPC .......... *A61L 27/3604* (2013.01); *A61K 35/35* (2013.01); *A61L 27/3683* (2013.01); *A61L 27/3687* (2013.01); *A61L 27/383* (2013.01); *A61L 27/3804* (2013.01); *A61L 27/3826* (2013.01); *A61L 27/3834* (2013.01); *A61L 27/54* (2013.01); *A61L 2300/414* (2013.01); *A61L 2400/12* (2013.01); *A61L 2430/40* (2013.01); *B82Y 5/00* (2013.01)

(58) Field of Classification Search
None
See application file for complete search history.

(56) References Cited

U.S. PATENT DOCUMENTS

| | | |
|---|---|---|
| 5,843,134 A | 12/1998 | Thong et al. |
| 6,600,956 B2 | 7/2003 | Maschino et al. |
| 2005/0013870 A1 | 1/2005 | Freyman et al. |
| 2006/0136028 A1 | 6/2006 | Ross et al. |
| 2007/0060815 A1 | 3/2007 | Martin et al. |
| 2007/0219642 A1 | 9/2007 | Richter |
| 2007/0248638 A1 | 10/2007 | Van Dyke et al. |
| 2008/0096005 A1 | 4/2008 | Premasiri |
| 2008/0208358 A1 | 8/2008 | Bellamkonda et al. |
| 2008/0260831 A1 | 10/2008 | Badylak et al. |
| 2009/0163990 A1 | 6/2009 | Yang et al. |
| 2009/0248113 A1 | 10/2009 | Nimer et al. |
| 2009/0280154 A1 | 11/2009 | Nielsen et al. |
| 2010/0094110 A1 | 4/2010 | Heller et al. |
| 2010/0106233 A1 | 4/2010 | Grant et al. |
| 2010/0114278 A1 | 5/2010 | McMorrow et al. |
| 2010/0211172 A1 | 8/2010 | Bellamkonda et al. |
| 2010/0255447 A1 | 10/2010 | Biris et al. |
| 2010/0273667 A1 | 10/2010 | Kotov et al. |
| 2011/0085968 A1 | 4/2011 | Jin et al. |
| 2011/0087315 A1 | 4/2011 | Richardson-Burns et al. |
| 2011/0143429 A1 | 6/2011 | Chun et al. |
| 2011/0306110 A1* | 12/2011 | Takeuchi ............. C12N 5/0075 435/178 |
| 2012/0177910 A1 | 7/2012 | Weber et al. |
| 2013/0085359 A1 | 4/2013 | Yao et al. |
| 2014/0145365 A1 | 5/2014 | Omenetto et al. |
| 2014/0271784 A1 | 9/2014 | Yang et al. |
| 2015/0202348 A1 | 7/2015 | Dvir et al. |
| 2015/0202351 A1 | 7/2015 | Kaplan et al. |
| 2016/0106886 A1 | 4/2016 | Dvir et al. |
| 2016/0270729 A1 | 9/2016 | Dvir et al. |
| 2018/0000990 A1 | 1/2018 | Dvir et al. |
| 2020/0101198 A1 | 4/2020 | Dvir et al. |

FOREIGN PATENT DOCUMENTS

| | | |
|---|---|---|
| EP | 2229191 | 9/2010 |
| WO | WO 2005/007233 | 1/2005 |
| WO | WO 2009/085547 | 7/2009 |

(Continued)

OTHER PUBLICATIONS

"Particle" definition. Merriam-Webster Online Dictionary. Accessed Dec. 9, 2019; https://www.merriam-webster.com/dictionary/particle (Year: 2019).*
Official Action dated Oct. 11, 2019 From the US Patent and Trademark Office Re. U.S. Appl. No. 15/037,129. (18 Pages).
Official Action dated Jan. 10, 2019 From the US Patent and Trademark Office Re. U.S. Appl. No. 15/702,834. (19 pages).
Official Action dated Dec. 27, 2019 From the US Patent and Trademark Office Re. U.S. Appl. No. 14/891,375. (32 pages).

(Continued)

*Primary Examiner* — Allison M Fox

(57) ABSTRACT

A spherical particle comprising decellularized omentum being between 1 nM-300 μM in diameter is disclosed. In some embodiments, the particle comprises biological cells. In other embodiments, the particle comprises a biomolecule. Uses of the particles are also disclosed.

9 Claims, 14 Drawing Sheets
(12 of 14 Drawing Sheet(s) Filed in Color)

(56) References Cited

FOREIGN PATENT DOCUMENTS

| WO | WO 2011/154424 | 12/2011 |
|----|----------------|---------|
| WO | WO 2011/159923 | 12/2011 |
| WO | WO 2012/094208 | 7/2012 |
| WO | WO 2013/086502 | 6/2013 |
| WO | WO 2013/109642 | 7/2013 |
| WO | WO 2014/037942 | 3/2014 |
| WO | WO 2014/188420 | 11/2014 |
| WO | WO 2014/207744 | 12/2014 |
| WO | WO 2015/048136 | 4/2015 |
| WO | WO 2015/071912 | 5/2015 |
| WO | WO 2017/103930 | 6/2017 |

OTHER PUBLICATIONS

Official Action dated Jan. 4, 2019 From the US Patent and Trademark Office Re. U.S. Appl. No. 14/891,375. (15 pages).
Official Action dated May 16, 2019 From the US Patent and Trademark Office Re. U.S. Appl. No. 15/702,834. (17 Pages).
International Preliminary Report on Patentability dated Dec. 3, 2015 From the International Bureau of WIPO Re. Application No. PCT/IL2014/050445.
International Preliminary Report on Patentability dated Jan. 7, 2016 From the International Bureau of WIPO Re. Application No. PCT/IL2014/050568.
International Preliminary Report on Patentability dated May 26, 2016 From the International Bureau of WIPO Re. Application No. PCT/IL2014/050994.
International Search Report and the Written Opinion dated Apr. 4, 2017 From the International Searching Authority Re. Application No. PCT/IL2016/051344. (12 Pages).
International Search Report and the Written Opinion dated Aug. 18, 2014 From the International Searching Authority Re. Application No. PCT/IL2014/050445.
International Search Report and the Written Opinion dated Mar. 22, 2015 From the International Searching Authority Re. Application No. PCT/IL2014/050994.
International Search Report and the Written Opinion dated Oct. 24, 2014 From the International Searching Authority Re. Application No. PCT/IL2014/050568.
Notice of Non-Compliant Amendment (37 CFR 1.121) dated May 5, 2015 From the US Patent and Trademark Office Re. U.S. Appl. No. 14/581,540.
Official Action dated Mar. 8, 2018 From the US Patent and Trademark Office Re. U.S. Appl. No. 14/891,375. (16 pages).
Official Action dated Mar. 13, 2017 From the US Patent and Trademark Office Re. U.S. Appl. No. 14/581,540. (15 pages).
Official Action dated Sep. 21, 2017 From the US Patent and Trademark Office Re. U.S. Appl. No. 14/891,375. (29 pages).
Official Action dated Jun. 28, 2016 From the US Patent and Trademark Office Re. U.S. Appl. No. 14/581,540.
Restriction Official Action dated Jul. 13, 2017 From the US Patent and Trademark Office Re. U.S. Appl. No. 14/891,375. (9 pages).
Supplementary European Search Report and the European Search Opinion dated Jun. 22, 2017 From the European Patent Office Re. Application No. 14862849.8. (12 Pages).
Supplementary European Search Report and the European Search Opinion dated Nov. 28, 2016 From the European Patent Office Re. Application No. 14800309.8. (7 Pages).
Aregueta-Robles et al. "Organic Electrode Coatings for Next-Generation Neural Interfaces", Frontiers in Neuroengineering, 7(Art. 15): 1-7, May 27, 2014. Abstract, Fig. 1.
Broda et al. "A Chemically Polymerized Electrically Conducting Composite of Polypyrrole Nanoparticles and Polyurethane for Tissue Engineering", Journal of Biomedical Materials Research, 98(4): 509-516, Sep. 15, 2011.
Cohen-Karni et al. "Nanocomposite Gold-Silk Nanofibers", Nano Letters, 12(10): 5403-5406, Aug. 28, 2012.
Cohen-Karni et al. "Nanocomposite Gold-Silk Nanofibers", Nano Letters, 12(10): 5403-5406, Aug. 28, 2012. Fig.1B.

Crapo et al. "An Overview of Tissue and Whole Organ Decellularization Processes", Biomaterials, 32(12): 3233-3243, Apr. 30, 2011.
Dvir et al. "Activation of the ERK1/2 Cascade Via Pulsatile Interstitial Fluid Flow Promotes Cardiac Tissue Assembly", Tissue Engineering, 13(9): 2185-2193, Sep. 2007.
Dvir et al. "Nanowired Three-Dimensional Cardiac Patches", Nature Nanotechnology, 6: 720-725, Nov. 2011.
Dvir et al. "Nanowired Three-Dimensional Cardiac Patches", Nature Nanotechnology, 6: 720-725, Published Online Sep. 25, 2011.
Dvir et al. "Prevascularization of Cardiac Patch on the Omentum Improves Its Therapeutic Outcome", Proc. Natl. Acad. Sci. USA, PNAS, 106(35): 14990-14995, Sep. 1, 2009.
Engelmayr Jr. et al. "Accordion-Like Honeycombs for Tissue Engineering of Cardiac Anisotropy", Nature Materials, 7(12): 1003-1010, Dec. 2008.
Fleischer et al. "Albumin Fiber Scaffolds for Engineering Functional Cardiac Tissues", Biotechnology and Bioengineering, 111(6): 1246-1257, Jun. 2014.
Fleischer et al. "Coiled Fiber Scaffolds Embedded With Gold Nanoparticles Improve the Performance of Engineered Cardiac Tissues", Nanoscale, 6(16): 9410-9414, Aug. 21, 2014.
Fleischer et al. "Spring-Like Fibers for Cardiac Tissue Engineering", Biomaterials, 34(34): 8599-8606, Available Online Aug. 13, 2013.
Gilbert et al. "Decellularization of Tissues and Organs", Biomaterials, XP002730648, 27: 3675-3683, 2006. p. 3676, Para 2, Table 1, p. 3679, Para 3.
Homola "Surface Plasmon Resonance Sensors for Detection of Chemical and Biological Species", Chemical Reviews, 108(2): 462-493, Jan. 30, 2008.
Hsu et al. "Gold Nanoparticles Induce Surface Morphological Transformation in Polyurethane and Affect the Cellular Response", Biomacromolecules, 9(1): 241-248, Jan. 2008.
Johnson et al. "Tailoring Material Properties of A Nanofibrous Extracellular Matrix Derived Hydrogel", Nanotechnology, 22(49): 494015-1-494015-23, Published Online Nov. 21, 2011.
Porzionato et al. "Decellularization of Rat and Human Omentum to Develop Novel Scaffolds to Be Recellularized With Adipose Derived Stem Cells", Italian Journal of Anatomy and Embryology, IJAE, 116(1/Suppl.): 149, 2011.
Porzionato et al. "Decellularized Omentum as Novel Biologic Scaffold for Reconstructive Surgery and Regenerative Medicine", European Journal of Histpchemistry, 57(e4): 24-30, 2013.
Prabhakaran et al. "Electrospun Composite Scaffolds Containing Poly(Octanediol-CO-Citrate) for Cardiac Tissue Engineering", Biopolymers. 97(7): 529-538, Feb. 10, 2012.
Prabhakaran et al. "Electrospun Composite Scaffolds Containing Poly(Octanediol-CO-Citrate) for Cardiac Tissue Engineering", Biopolymers, 97(7): 529-538, Published Online Feb. 10, 2012.
Radisic et al. "Functional Assembly of Engineered Myocardium by Electrical Stimulation of Cardiac Myocytes Cultured on Scaffolds", Proc. Natl. Acad. Sci. USA, PNAS, 101(52): 18129-18134, Dec. 28, 2004.
Sawkins et al. "Hydrogels Derived From Demineralized and Decellularized Bone Extracellular Matrix", Acta Biomaterialia, 9: 7865-7873, 2013.
Sawkins et al. "Hydrogels Derived From Demineralized and Decellularized Bone Extracellular Matrix", Acta Biomaterialia, XP002730649, 9(8): 7865-7873, Available Online Apr. 25, 2013. p. 7866, 1-h col. Para 2, r-h col. Para 6, p. 7867, 1-h col. Para 6.
Shevach et al. "Fabrication of Omentum-Based Matrix for Engineering Vascularized Cardiac Tissues", Biofabrication, 6(2): 024101-1-024101-12, Published Online Jan. 24, 2014. Para 4.1, p. 9, Fig.8.
Shevach et al. "Gold Nanoparticle-Decellularized Matrix Hybrids for Cardiac Tissue Engineering", Nano Letters, 14(10): 5792-5796, Sep. 8, 2014.
Shevach et al. "Nanoengineering Gold Particle Composite Fibers for Cardiac Tissue Engineering", Journal of Materials Chemistry B, 1(39): 5110-5217, 2013.
Shevach et al. "Omentum ECM-Based Hydrogel as A Platform for Cardiac Cell Delivery", Biomedical Materials, 10(3): 034106-1-034106-11, May 13, 2015. Para 2.1, p. 2, Fig.7.

(56) References Cited

OTHER PUBLICATIONS

Singelyn et al. "Catheter-Deliverable Hydrogel Derived From Decellularized Ventricular Extracellular Matrix Increases Endogenous Cardiomyocytes and Preserves Cardiac Function Post-Myocardial Infarction", Journal of the American College of Cardiology, JACC, 59(8): 751-763, Feb. 21, 2012.

Soffer-Tztir et al. "Optimizing the Biofabrication Process of Omentum-Based Scaffolds for Engineering Autologous Tissues", Biofabrication, 6(3): 035023-1-035023-14, Published Online Aug. 27, 2014. Table 1.

Tian et al. "Macroporous Nanowire Nanoelectronic Scaffolds for Synthetic Tissues", Nature Materials, 11: 986-994, Nov. 2012 & Supplementary Information, p. 1-27, 2012.

Whelove et al. "Development and In Vitro Studies of A Polyethylene Terephthalate-Gold Nanoparticle Scaffold for Improved Biocompatibility", Journal of Biomedical Materials Research, Part B: Applied Biomaterials, 99B(1): 142-149, Oct. 2011.

Whelove et al. "Development and In Vitro Studies of A Polyethylene Terephthalate-Gold Nanoparticle Scaffold for Improved Biocompatibility", Journal of Biomedical Materials Research, Part B: Applied Biomaterials, 99B(1): 142-149, Published Online Jul. 28, 2011.

You et al. "Nanoengineering the Heart: Conductive Scaffolds Enhance Connexin 43 Expression", Nano Letters, 11(9): 3643-3648, Aug. 1, 2011.

Zhang et al. "Neurite Development in PC12 Cells on Nanostructured Substrates", Advances in Science and Technology, 53: 85-90, Oct. 1, 2006.

Zimmermann et al. "Tissue Engineered of A Differential Cardiac Muscle Construct", Circulation Research, 90(2): 223-230, Feb. 8, 2002.

Official Action dated Mar. 21, 2019 From the US Patent and Trademark Office Re. U.S. Appl. No. 15/037,129. (38 pages).

Supplementary European Search Report and the European Search Opinion dated Jul. 22, 2019 From the European Patent Office Re. Application No. 16875065.1. (8 Pages).

Mao et al. "Recent Advances in Polymeric Microspheres for Parental Drug Delivery—Part 2", Expert Opinion on Drug Delivery, XP055605149, 9(10): 1209-1223, Aug. 28, 2012.

Yao et al. "Collagen Microsphere Serving as A Cell Carrier Supports Oligodendrocyte Progenitor Cell Growth and Differentiation for Neurite Myelination In Vivo", Stem Cell Research & Therapy, XP021162904, 4(5): 109-1-109-8, Sep. 9, 2013.

Communication Pursuant to Article 94(3) EPC dated May 29, 2020 From the European Patent Office Re. Application No. 16875065.1. (8 Pages).

Collins et al. "The Poisson Distribution and Beyond: Methods for Microfluidic Droplet Production and Single Cell Encapsulation", Lab on A Chip, XP055426432, 15(17): 3439-3459, Published Online Jul. 30, 2015.

Official Action dated Jun. 11, 2020 from the US Patent and Trademark Office Re. U.S. Appl. No. 15/037,129. (21 pages).

Achyuta et al. "Biocompatibility Assessment of Insulating Silicone Polymer Coatings Using an in vitro Glial Scar Assay", Macromolecular Bioscience 10: 872-880, 2010.

Final Official Action dated Oct. 16, 2020 From the US Patent and Trademark Office Re. U.S. Appl. No. 14/891,375. (19 pages).

\* cited by examiner

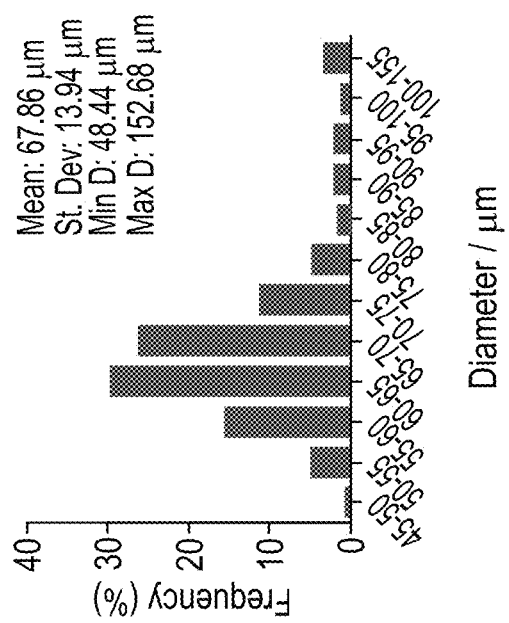

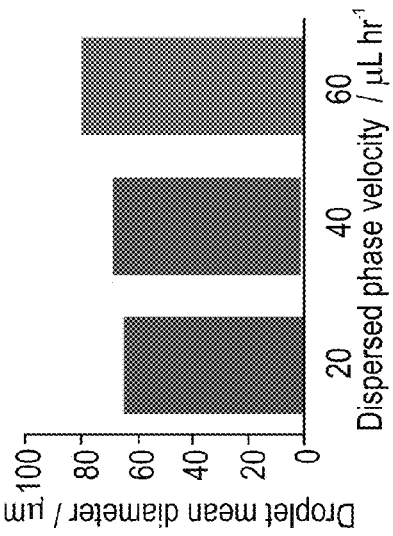
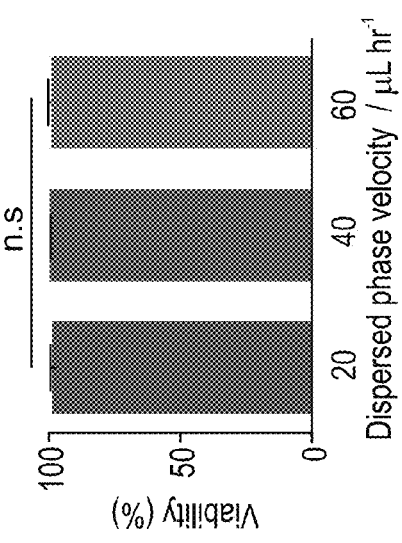
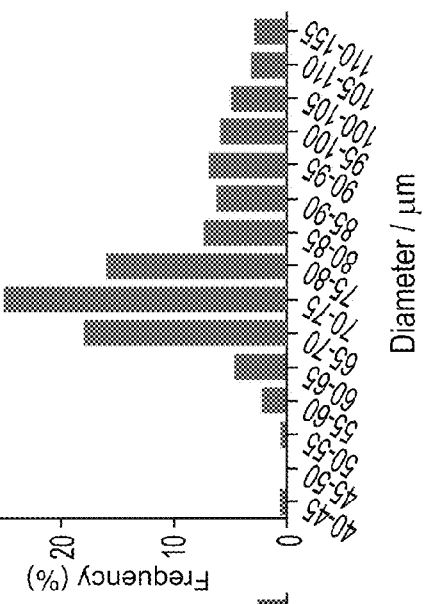
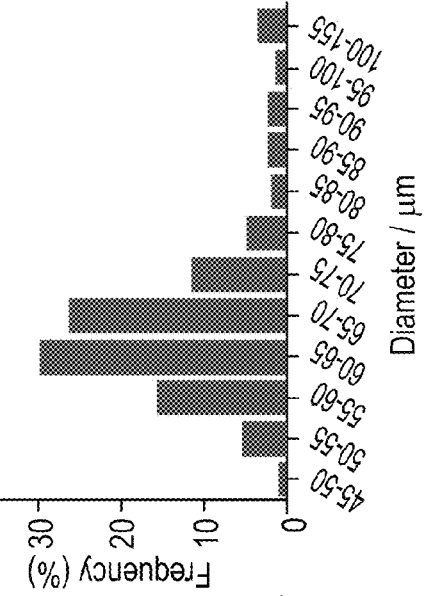
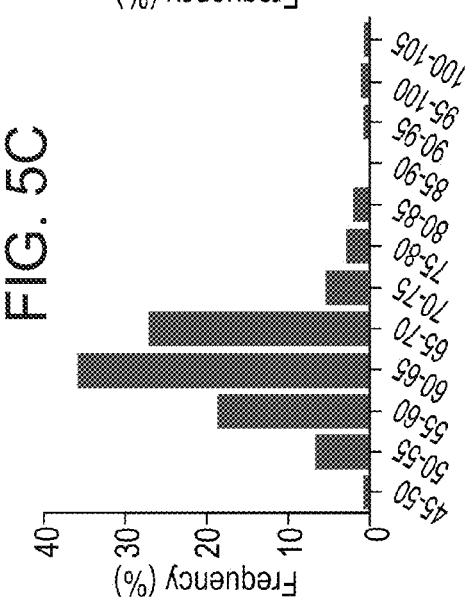

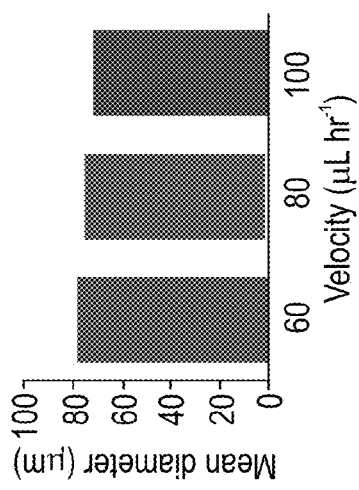
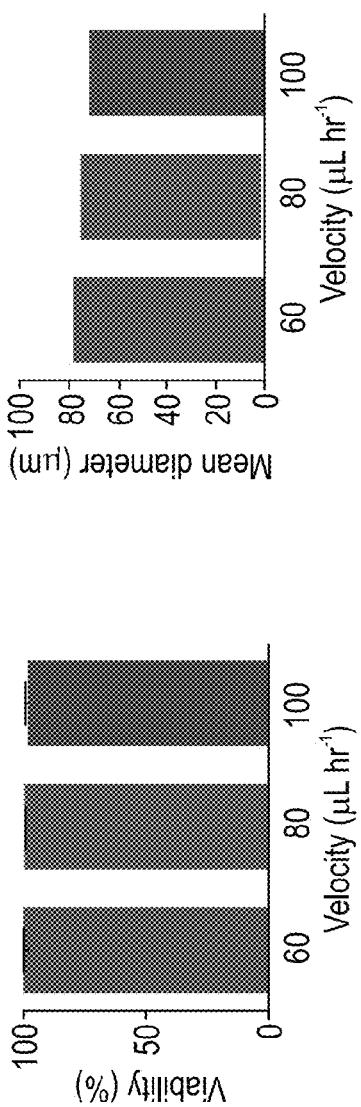
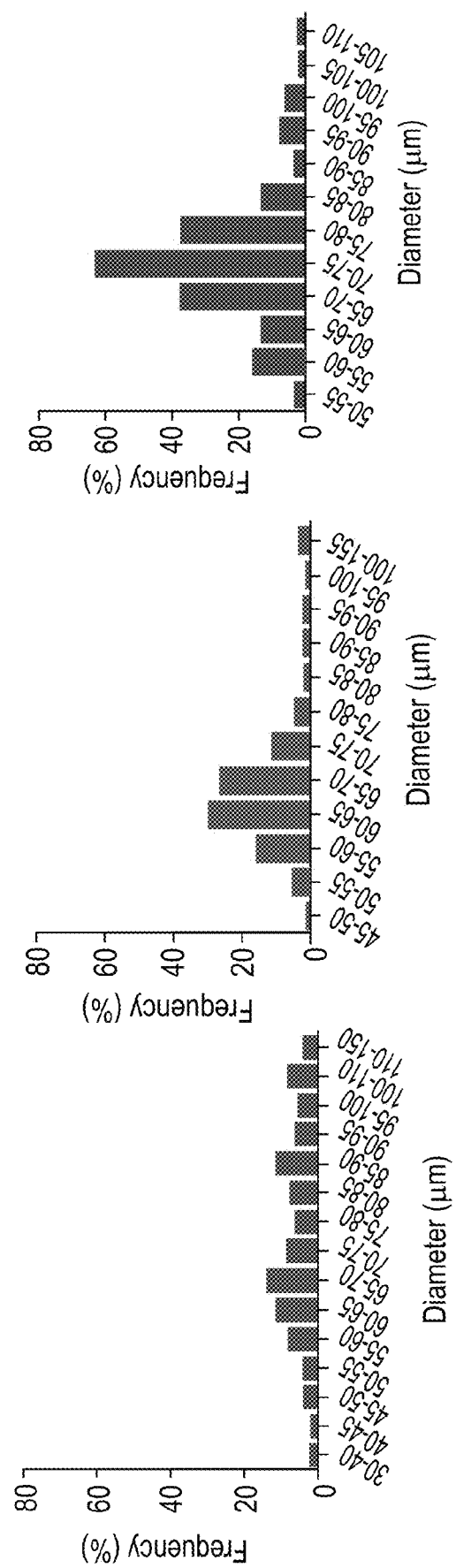

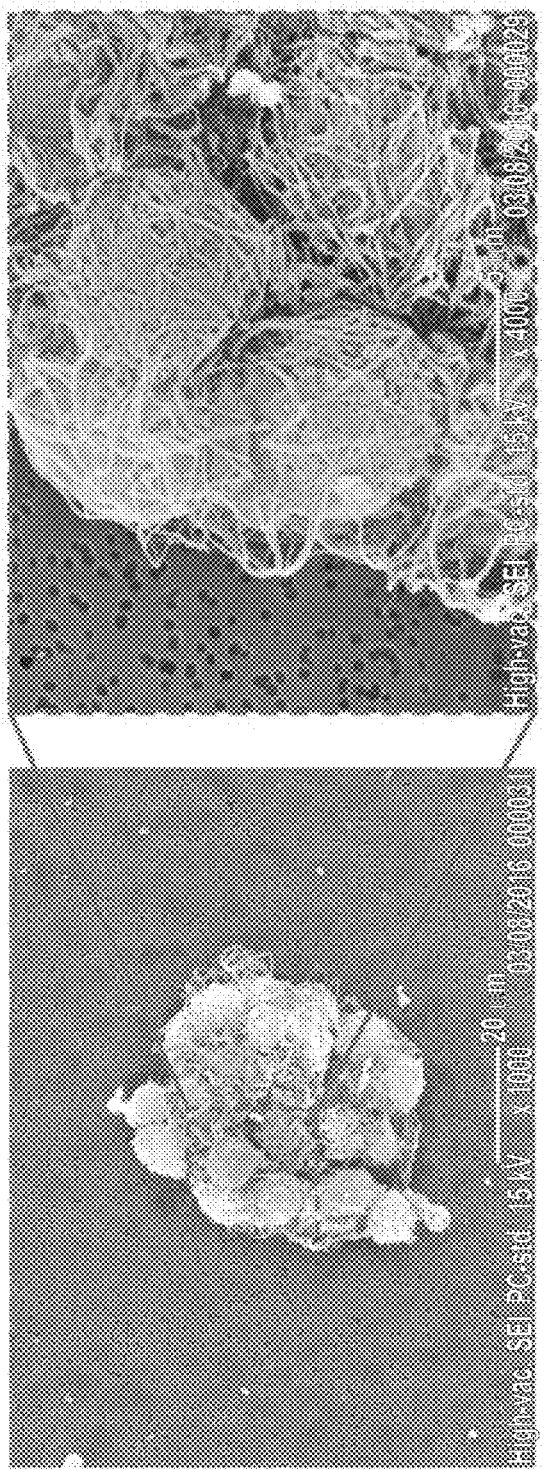
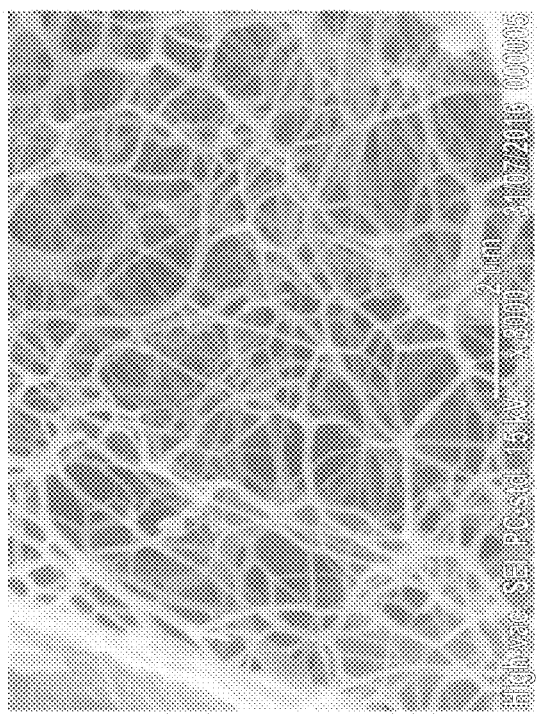

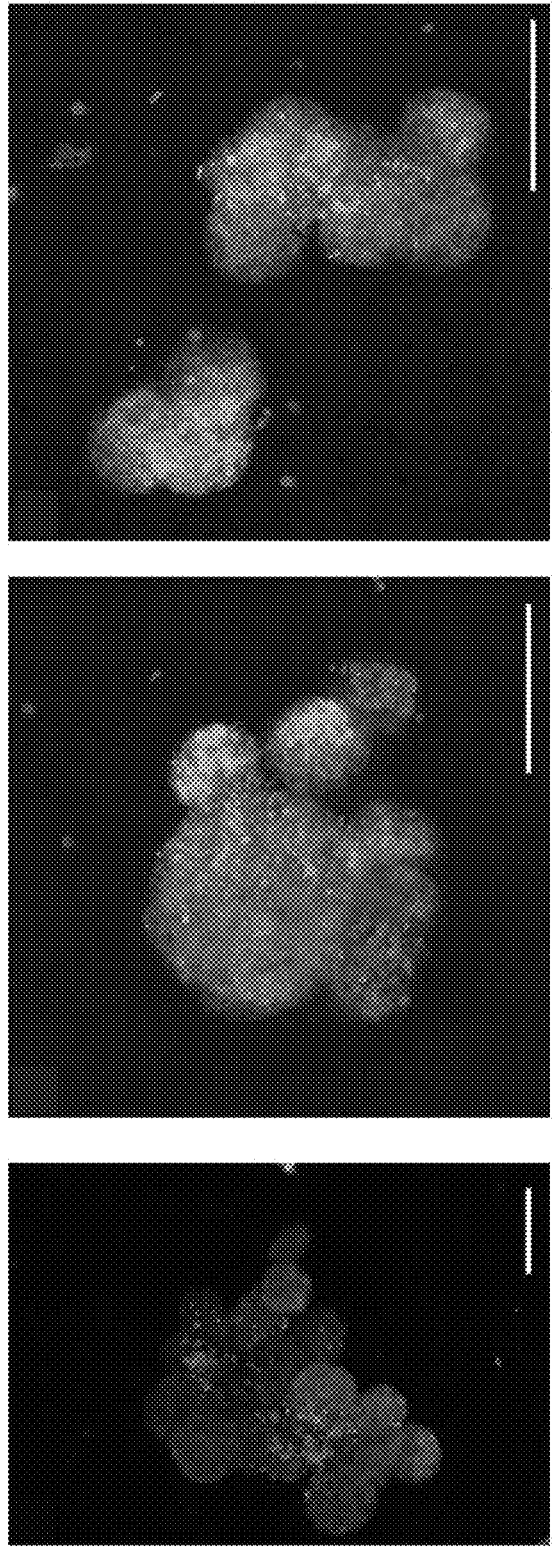

US 11,213,609 B2

PARTICLES COMPRISING DECELLULARIZED OMENTUM

RELATED APPLICATIONS

This application is a National Phase of PCT Patent Application No. PCT/IL2016/051344 having International filing date of Dec. 15, 2016, which claims the benefit of priority under 35 USC § 119(e) of U.S. Provisional Patent Application No. 62/268,046 filed on Dec. 16, 2015. The contents of the above applications are all incorporated by reference as if fully set forth herein in their entirety.

FIELD AND BACKGROUND OF THE INVENTION

The present invention, in some embodiments thereof, relates to particles comprising decellularized omentum. The particles may be used for cell and/or biomolecule delivery.

The omentum is a double sheet of peritoneum that extends from the greater curvature of the stomach overlying most abdominal organs. This tissue is highly vascularized and its fibrillar ECM is rich with collagens, adhesive proteins and GAGs. Since GAGs bind a variety of protein ligands, they can serve as growth factor depots and regulate a wide variety of biological activities, including developmental processes, angiogenesis, and cardioprotection. Due to its unique composition, the omentum also serves as a depot for adult stem cells with regenerative potential. These stem cells are based in the omentum matrix and upon signals migrate to heal injured organs. The overall regenerative capacity of the omentum, its ability to maintain progenitor cell viability, absorb large amounts of edema fluids and limit the formation of scar tissue at the site of injury, has long been demonstrated.

Dvir, T., et al. (Proc Natl Acad Sci USA 106, 14990-14995 (2009)) teaches the utilization of the omentum to induce cell migration and blood vessel network formation in an implanted synthetic scaffold. These vascularized scaffolds were then re-implanted on the infarcted heart and completely attenuated its deterioration.

International Patent Application No. WO2009/085547 teaches the generation of decellularized omentum scaffolds for tissue engineering.

U.S. Patent Publication No. 20050013870 teaches a scaffold comprising decellularized extracellular matrix of a number of body tissues including omentum. The body tissues have been conditioned to produce a biological material such as a growth factor.

U.S. Patent Publication No. 20090163990 teaches methods of decellularizing omentum.

U.S. Patent Publication No. 20150202348 teaches decellularized omentum for tissue engineering.

Porzionato et al. (Italian Journal of Anatomy and Embryology, Volume 116, 2011 and Eur J Histochem. 2013 Jan. 24; 57(1):e4. doi: 10.4081/ejh.2013.e4) teaches decellularized omentum.

Soluble forms of decellularized extracellular matrix are known in the art as described in Acta Biomaterialia, Volume 9, Issue 8, August 2013, Pages 7865-7873 and Singelyn et al., J Am Coll Cardiol. Feb. 21, 2012; 59(8): 751-763.

Additional background art includes WO2014/037942, Gilbert et al., Biomaterials 27 (2006) 3675-3683 and Flynn et al., Biomaterials 31 (2010), 4715-4724.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

SUMMARY OF THE INVENTION

According to an aspect of some embodiments of the present invention there is provided a spherical particle comprising decellularized omentum being between 1 nM -300 µM in diameter.

According to an aspect of some embodiments of the present invention there is provided a composition comprising:
  (i) a plurality of the particles described herein; and
  (ii) biological cells and/or at least one biomolecule.

According to an aspect of some embodiments of the present invention there is provided a method of generating particles comprising decellularized omentum comprising:
  (a) dispersing a composition comprising solubilized decellularized omentum in an oil under conditions that allow generation of emulsified, decellularized omentum; and
  (b) heating the emulsified, decellularized omentum to generate solid particles of decellularized omentum, thereby generating particles comprising decellularized omentum.

According to an aspect of some embodiments of the present invention there is provided a method of treating a disease or medical condition which would benefit from cell transplantation in a subject in need thereof, comprising administering to the subject a therapeutically effective amount of a plurality of the particles described herein, thereby treating the medical condition.

According to some embodiments of the present invention, the particle is a microparticle.

According to some embodiments of the present invention, the particle is between 50-300 µm in diameter.

According to some embodiments of the present invention, the particle is a nanoparticle.

According to some embodiments of the present invention, more than 20% of the particle is composed of decellularized omentum.

According to some embodiments of the present invention, the omentum comprises human omentum.

According to some embodiments of the present invention, the particle encapsulates at least one biological cell.

According to some embodiments of the present invention, the biological cell is selected from the group consisting of a cardiac cell, a neuronal cell, a pancreatic cell, a stem cell, a liver cell, a muscle cell, a blood cell and an immune cell.

According to some embodiments of the present invention, the particle encapsulates at least one biomolecule.

According to some embodiments of the present invention, the particle further encapsulates at least one biomolecule.

According to some embodiments of the present invention, the biomolecule is selected from the group consisting of bone morphogenetic protein-2 (BMP-2), bone morphogenetic protein-7 (BMP-7), transforming growth factor beta (TGF-β), interleukin 10 (IL10), vascular endothelial growth factor (VEGF), Insulin-like growth factor (IGF-1), stromal cell derived factor-1 (SDF-1), platelet derived growth factor (PDGF), neurotrophin (NT-3), dexamethasone, noradrenaline, keratinocyte growth factor (KGF), angioprotein (Ang-1), fibroblast growth factor (FGF-2) and nerve growth factor (NGF).

According to some embodiments of the present invention, each of the particles of the plurality of particles are of substantially the same size.

According to some embodiments of the present invention, the particles encapsulate the biological cells and/or at least one biomolecule.

According to some embodiments of the present invention, the biological cells are selected from the group consisting of cardiac cells, neuronal cells, pancreatic cells, stem cells, liver cells, and muscle cells.

According to some embodiments of the present invention, the at least one biomolecule is selected from the group consisting of bone morphogenetic protein-2 (BMP-2), bone morphogenetic protein-7 (BMP-7), transforming growth factor beta (TGF-β), interleukin 10 (IL10), vascular endothelial growth factor (VEGF), Insulin-like growth factor (IGF-1), stromal cell derived factor-1 (SDF-1), platelet derived growth factor (PDGF), neurotrophin (NT-3), dexamethasone, noradrenaline, keratinocyte growth factor (KGF), angioprotein (Ang-1), fibroblast growth factor (FGF-2) and nerve growth factor (NGF).

According to some embodiments of the present invention, the method further comprises separating the solid particles comprising decellularized omentum from the oil following the heating.

According to some embodiments of the present invention, the heating is effected at about 37° C.

According to some embodiments of the present invention, the oil is a fluorinated oil.

According to some embodiments of the present invention, the fluorinated oil is selected from the group consisting of FC-40, FC-770, FC-70, FC-77, FC-72, FC-43, FC-3283, FC-3284, perfluoro-hexane (PFH), perfluoro-cyclohexane (PFC), perfluoro-decaline (PFD), perfluoro-perhydrophenanthrene (PFPH) and Novec/hydrofluoroether (HFE)-7500/7100/7200/71DA/71DE/71IPA/72DA/72DE.

According to some embodiments of the present invention, the oil is a hydrocarbon oil.

According to some embodiments of the present invention, the hydrocarbon oil is selected from the group consisting of light mineral oil, heavy mineral oil, hexadecane, tetradecane, octadecane, dodecane, Isopar™ Isoparaffinic fluids and vegetable oil.

According to some embodiments of the present invention, the composition further comprises a surfactant.

According to some embodiments of the present invention, the surfactant is selected from the group consisting of pico-surf™ 1, pico-surf™ 2, perfluoro (PF)-octanol, PF-decanol, PF-tetradecanoic (TD) acid, PF-TD OEG, perfluoropolyether (PFPE)-COOH, PFPE-COONH4, PFPE-PEG, PFPE-DMP, perfluoro-short chains.

According to some embodiments of the present invention, the separating the solid particles of decellularized omentum from the oil is effected by contacting the solid particles with a hydrophilic solution.

According to some embodiments of the present invention, the separating is effected using a microfluidics device.

According to some embodiments of the present invention, the separating is effected using a 3D printer.

According to some embodiments of the present invention, the method further comprises sonicating the solid particles following the separating.

According to some embodiments of the present invention, the composition further comprises at least one biological cell.

According to some embodiments of the present invention, the at least one biological cell is selected from the group consisting of a cardiac cell, a neuronal cell, a pancreatic cell, a stem cell, a liver cell, a muscle cell.

According to some embodiments of the present invention, the composition further comprises a biomolecule.

According to some embodiments of the present invention, the biomolecule is a growth factor.

According to some embodiments of the present invention, the biomolecule is a neuropeptide.

According to some embodiments of the present invention, the biomolecule is a neurotransmitter.

According to some embodiments of the present invention, the omentum comprises human omentum.

According to some embodiments of the present invention, the method further comprises crosslinking the particles following the separating.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
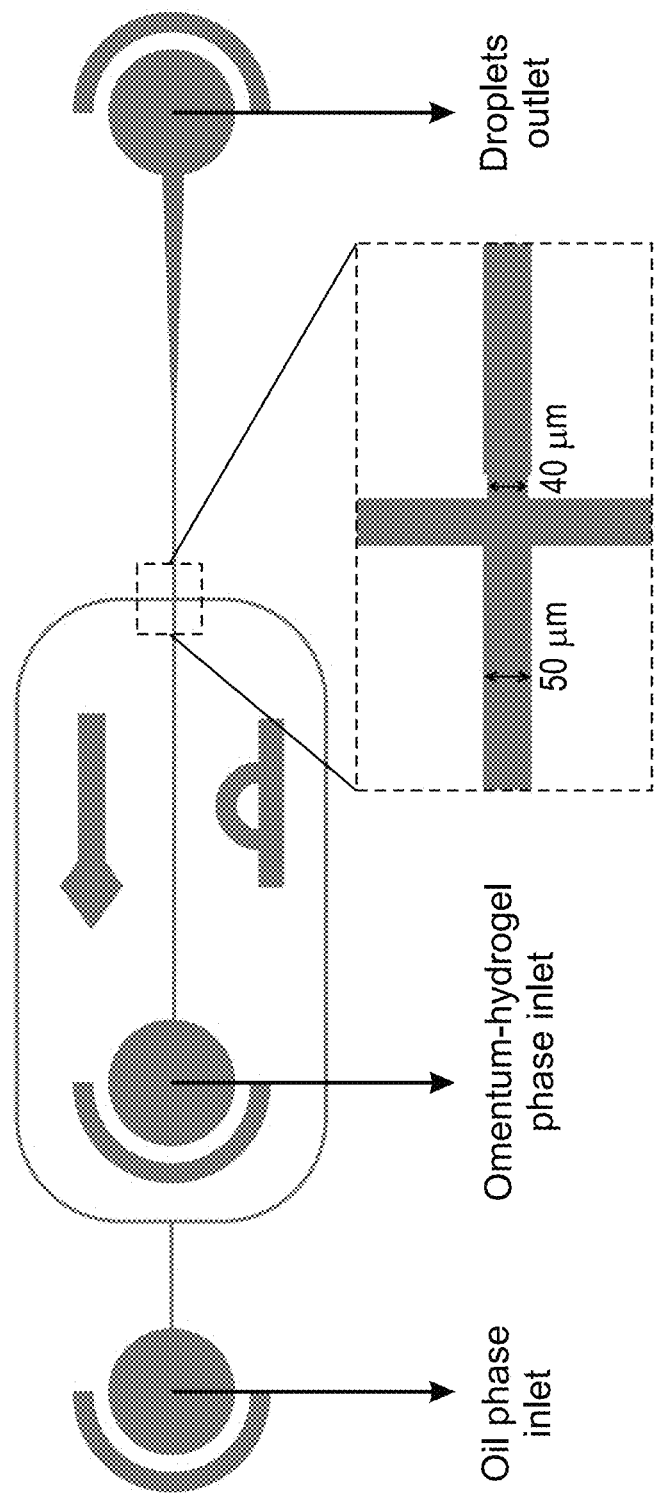

FIG. 1 is a scheme of an exemplary microfluidic device. The omentum-gel stream is dispersed by the continuous phase, the oil stream, to produce omentum-gel droplets. According to some embodiments, all microfluidics channels are 25 μm wide and high. According to other embodiments, the microfluidics channels are 50 μm in width and height, except for the nozzle (at the zone where the droplets are produced) are 40 μm in width.

Figure 2:
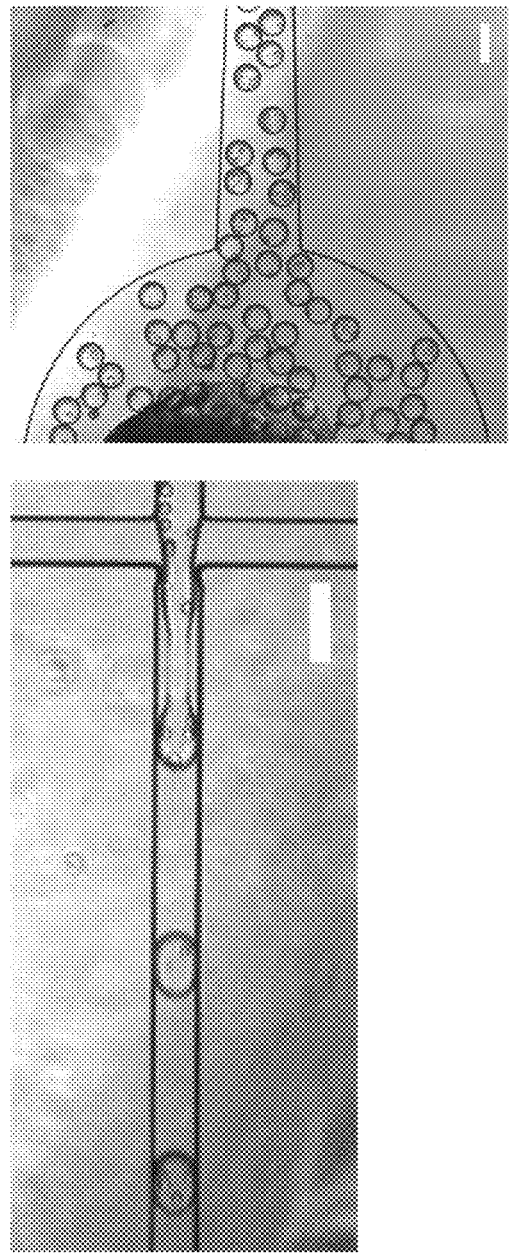

FIGS. 2A-B are bright field (BF) images of the device droplets generation zone (FIG. 2A) and the device outlet region of droplets (FIG. 2B). Cells can be observed within the droplets. Bar-100 μm.

Figure 3:
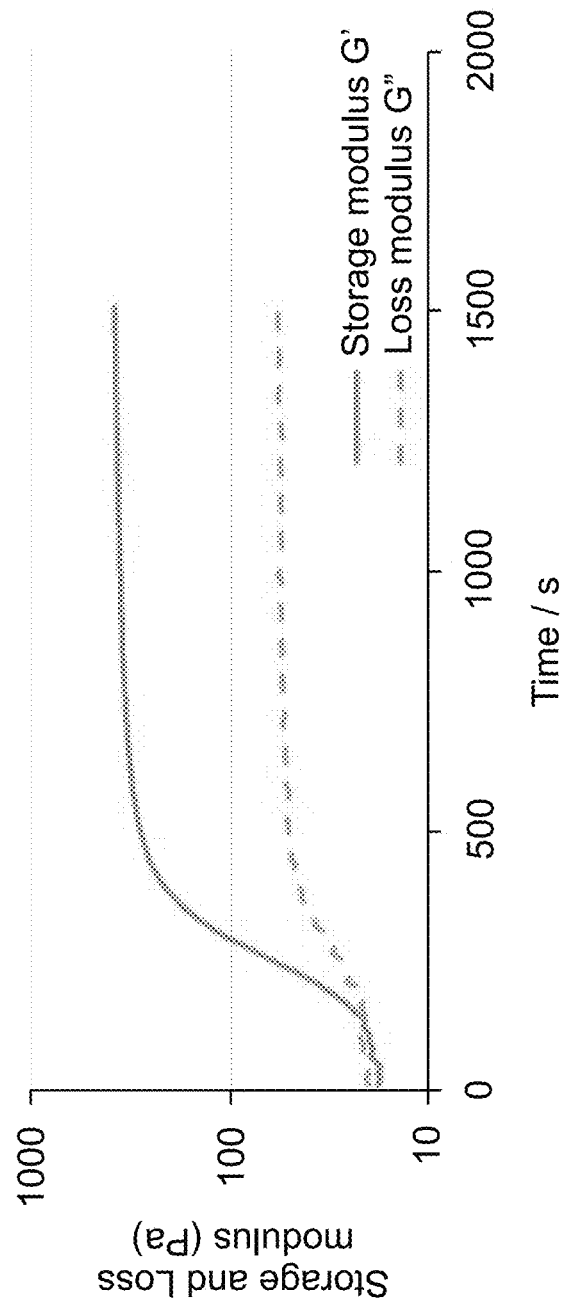

FIG. 3 is a graph illustrating the rheological properties of omentum-hydrogel. Representative curves of storage (G', consecutive line) and the loss modulus (G", dashed line) during gelation at 37° C.

FIGS. 4A-C illustrate viability (FIG. 4A) and size distribution of encapsulated 3T3 fibroblasts cells using 5% (FIG.

4B) and 2% (FIG. 4C) pico-surf™2 surfactant. Continuous phase velocity—80 μl hr$^{-1}$, dispersed phase velocity—40 μl hr$^{-1}$.

FIGS. 5A-E are graphs illustrating cell viability (FIG. 5A), droplet mean diameter (FIG. 5B) and droplet size distribution of encapsulated 3T3 fibroblasts cells using 20 (FIG. 5C), 40 (FIG. 5D) and 60 (FIG. 5E) μl hr$^{-1}$ dispersed phase velocity. Continuous phase velocity—80 μl hr$^{-1}$.

Figure 6B:
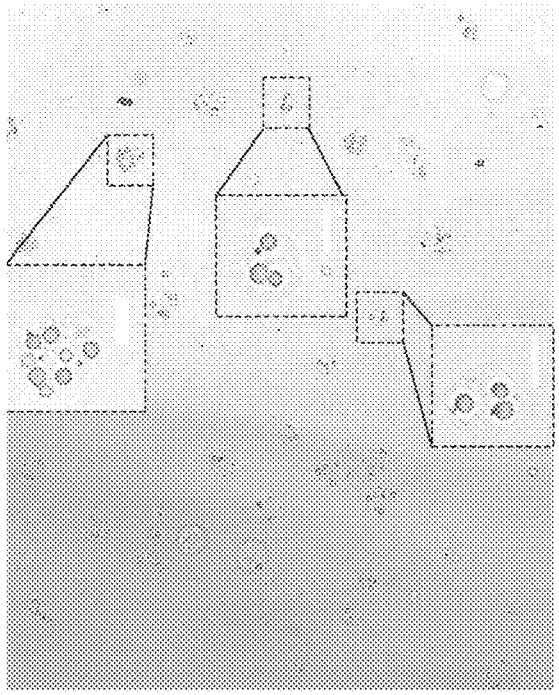
Figure 6A:
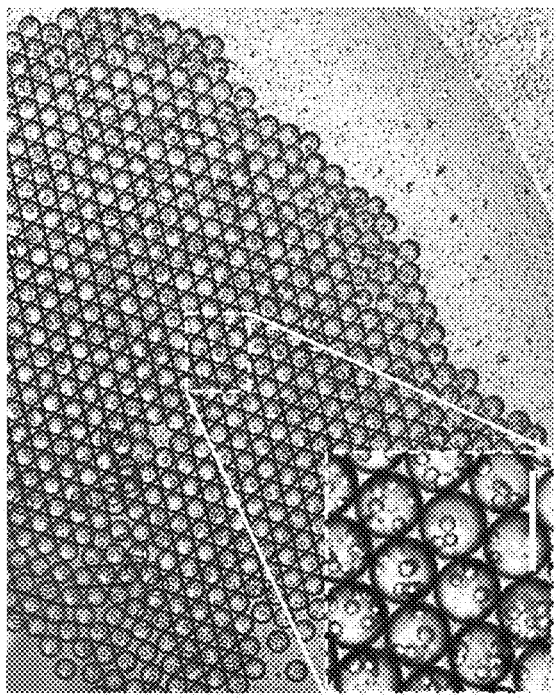

FIGS. 6A-B are photographs of encapsulated cells. (FIG. 6A) BF image of 3T3 fibroblasts cells immediately after encapsulation (dispersed phase velocity—20 μl hr$^{-1}$, bar-100 μm) and (B) Fluorescence image of live (green) and dead (red) cells in aqueous medium (dispersed phase velocity 60 μl hr$^{-1}$). Bar-100 μm, bar of enlarged images—50 μm. Continuous phase velocity in (A) and (B) 80 μl hr$^{-1}$.

FIGS. 7A-E are graphs illustrating cell viability (FIG. 7A), droplet mean diameter (FIG. 7B) droplet size distribution of encapsulated 3T3 fibroblasts cells using 60 (FIG. 7C) 80 (FIG. 7D) and 100 (FIG. 7E) μl hr$^{-1}$ continuous phase velocity. Dispersed phase velocity—40 μl hr$^{-1}$.

Figure 8A:
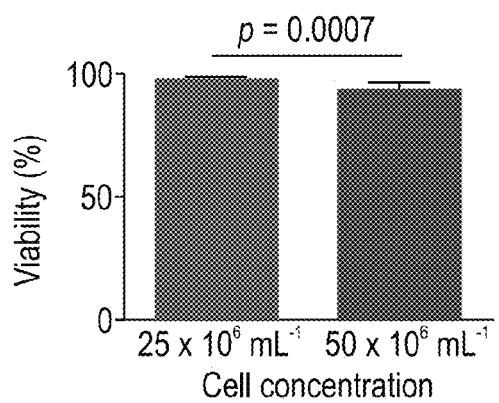
Figure 8B:
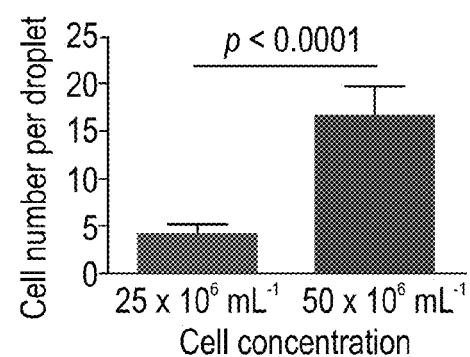
Figure 8C:
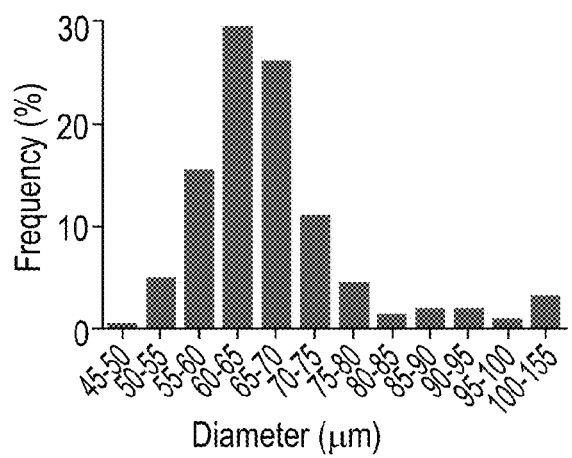
Figure 8D:
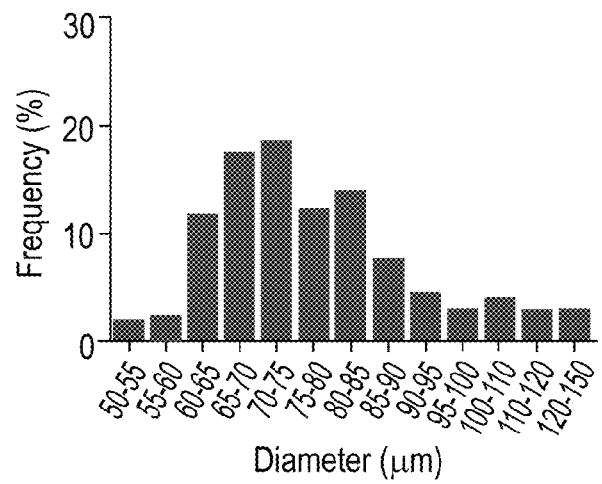
Figure 8E:
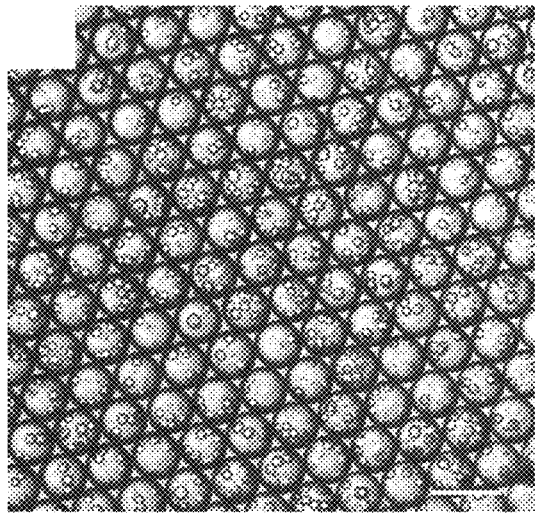
Figure 8F:
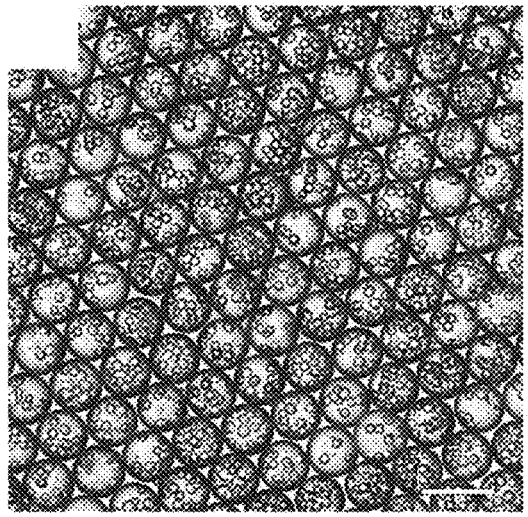
Figure 11A:
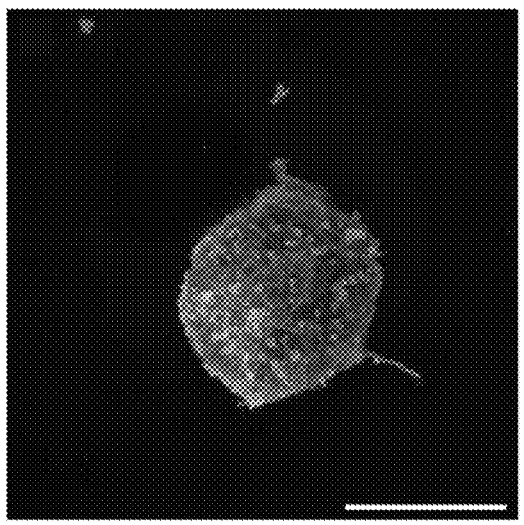
Figure 11B:
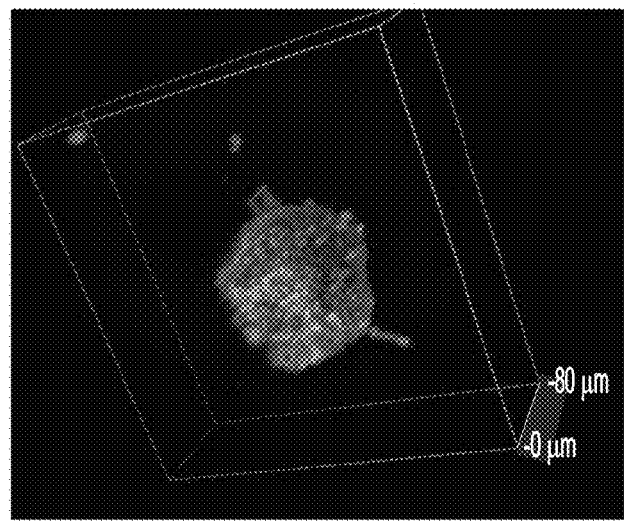
Figure 11C:
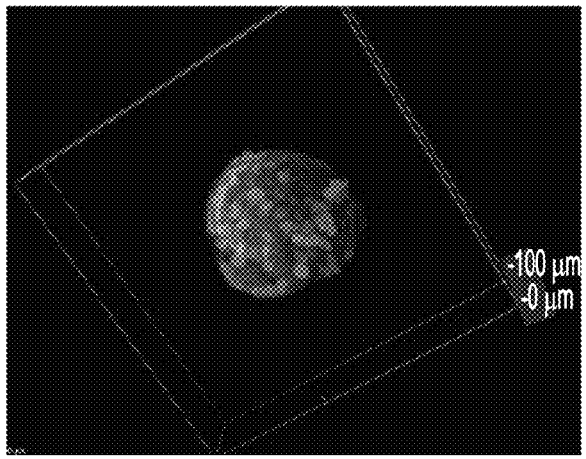
Figure 11D:
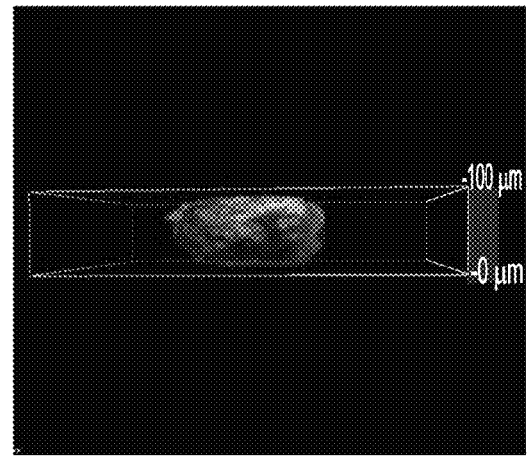

FIGS. 8A-F are graphs illustrating cell viability (FIG. 8A), cell number per droplet (FIG. 8B)) droplet size distribution (FIGS. 8C-D) and bright field image (FIGS. 8E-F) of encapsulated 3T3 fibroblasts cells using $25 \times 10^6$ mL$^{-1}$ (FIGS. 8C,E) and $50 \times 10^6$ mL$^{-1}$ (FIGS. 8D,F). Scale bar (FIGS. 8E-F)—100 μm. Dispersed phase velocity—40 μl hr$^{-1}$. Continuous phase velocity—80 μl hr$^{-1}$.

FIGS. 9A-C illustrate scanning electron microscopy of omentum-hydrogel droplets with (FIGS. 9A-B) and without (FIG. 9C) encapsulated 3T3 fibroblasts cells.

FIGS. 10A-C are immunofluorescence images of encapsulated spinal cord neurons (collagen stained green, nuclei stayed blue and β-tubulin stained red). Scale bar—100 μm.

FIGS. 11A-D are immunofluorescence images of encapsulated neonatal CMs (collagen stained green, nuclei stayed blue and α-actinin stained red), at day 8 (FIGS. 11A-B) and day 13 (FIGS. 11C-D) after encapsulation. Scale bar (A)—100 μm.

Figure 12B:
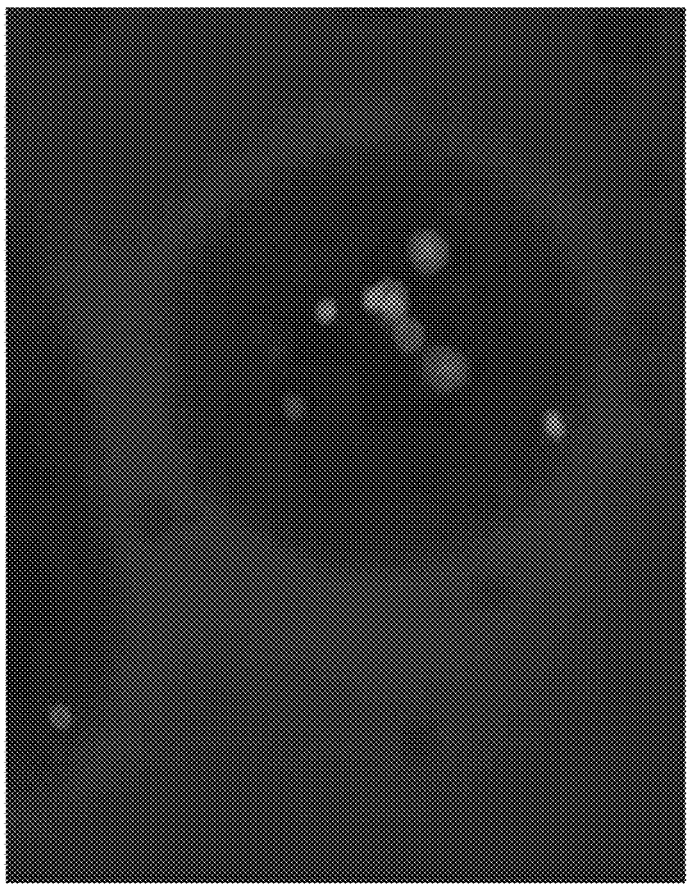
Figure 12A:
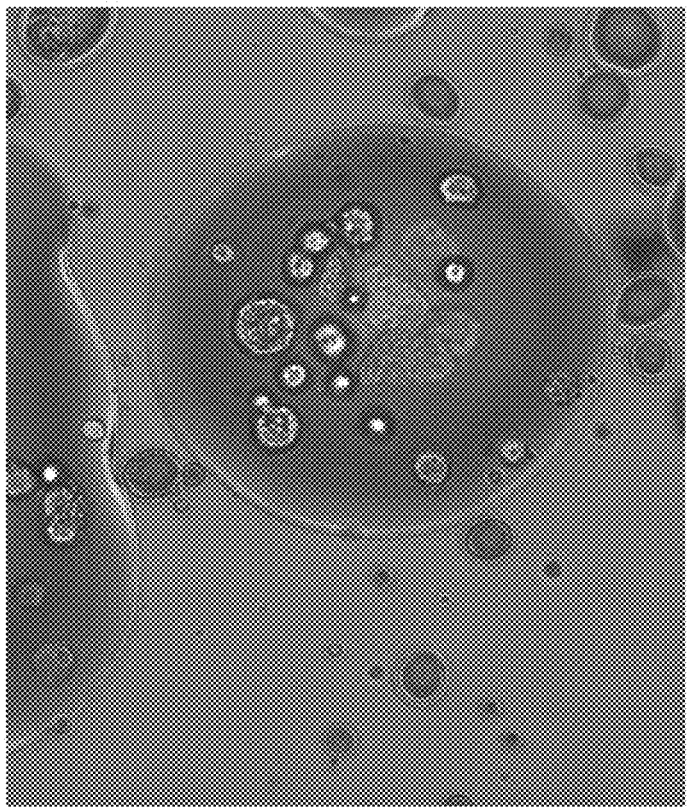

FIGS. 12A-B: Encapsulation of 3T3 fibroblasts in omentum-gel droplets using emulsion mixing. A. Bright field image of a droplet. B. Cell nuclei is visualized by fluorescence image of hoechst staining. 1% omentum-gel, containing 50,000 fibroblasts/ml, was dispersed in vacuum oil, 0.2% span 80.

Figure 13B:
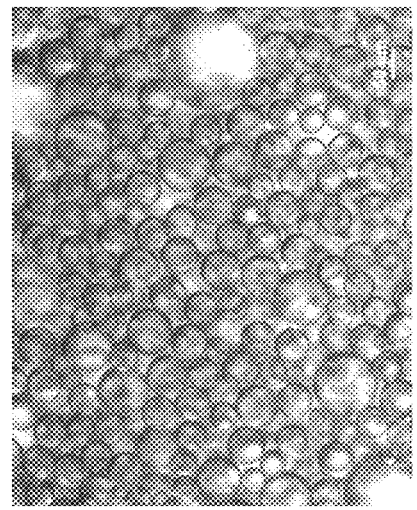
Figure 13A:
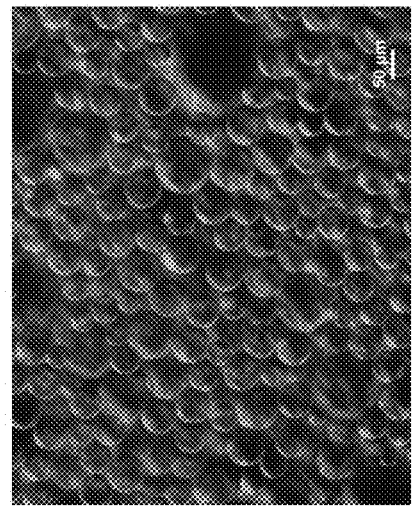

FIGS. 13A-B illustrate encapsulation of 3T3 fibroblasts in omentum-gel droplets generated using microfluidics. A. Bright field image of the droplets B. Droplets are visualized by fluorescence microscopy (green autofluorescence). 0.67% omentum-gel, containing 1,000,000 fibroblasts/ml, was dispersed in fluorinated-40 (FC-40) oil, 2% span 80.

Figure 14:
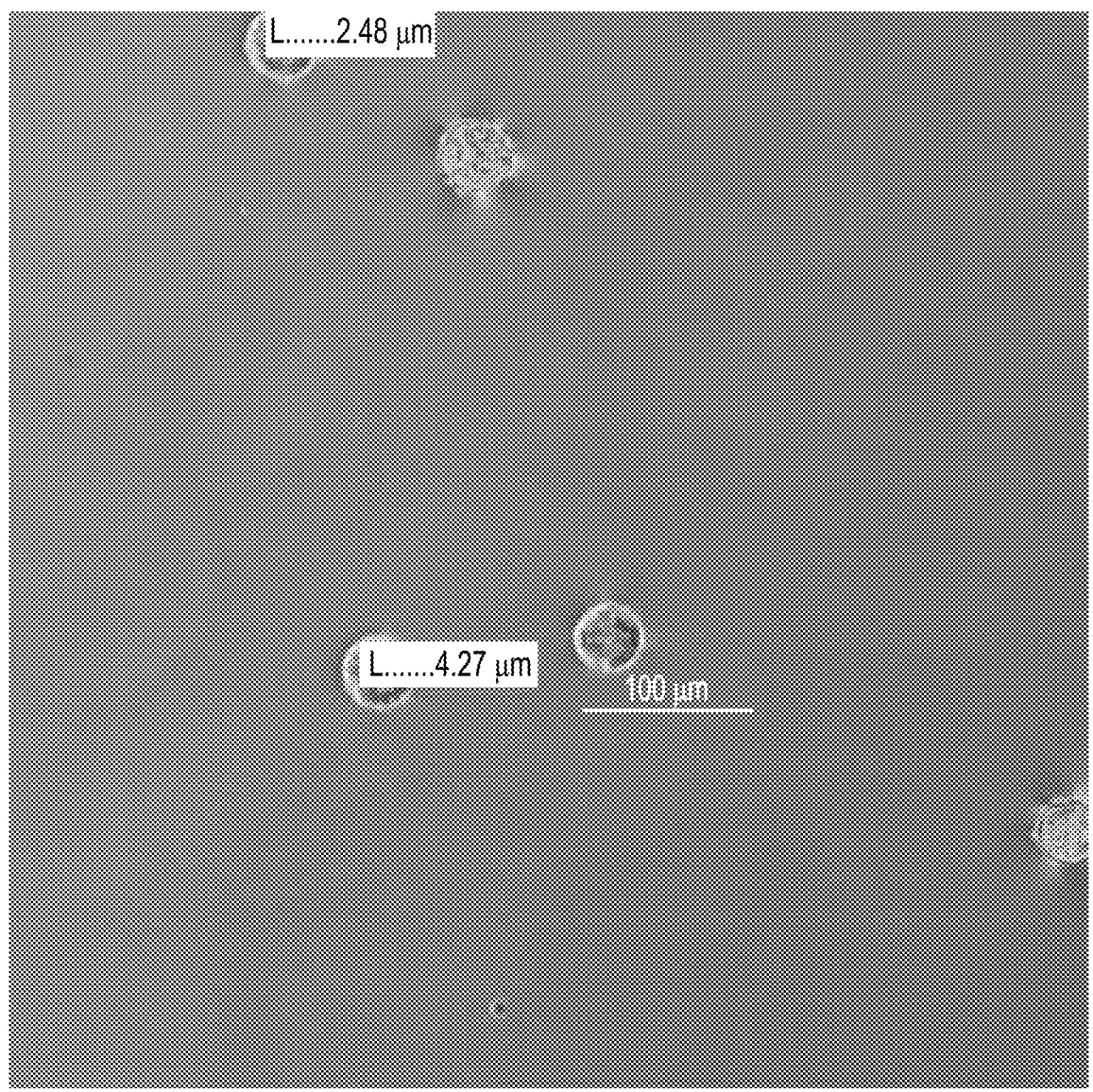

FIG. 14 illustrates 1% omentum-gel droplet production using 3D inkjet bio-printing. Droplets were very homogenous in size exhibiting approximately 40 μm diameter. The droplets were printed directly into heavy mineral oil.

DESCRIPTION OF SPECIFIC EMBODIMENTS OF THE INVENTION

The present invention, in some embodiments thereof, relates to particles comprising decellularized omentum. The particles may be used for cell and/or biomolecule delivery.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Encapsulating cells in hydrogels has shown promising results for reducing the immune response, but many preclinical and clinical trials results have been inconsistent because of the limited ability of hydrogels to support cellular viability and function over an extended time period. Therefore, few successful products have been fully commercialized based on these cell-encapsulation technologies.

The present inventors have now generated micro and nanoparticles made of autologous biomaterial originating from the omentum. The omentum was harvested from subjects via a simple laparoscopic procedure. Following decellularization using physical, chemical or/and enzymatic processing, the extracellular matrix (ECM) of the omentum was converted into a liquid substance that was emulsified to generate omentum-ECM particles that were thermoresponsive and gel upon incubation at 37° C. The present inventors have shown that cells and/or biomolecules (e.g. cytokines, growth factors, drugs etc.) and/or other nanoparticles may be entrapped in these particles (FIGS. 10A-C, 11A-D, 12A-B and 13A-B). Following gelation, the resulting particles may serve as vehicles for protection and release of the cargo for various applications such as tissue engineering and regeneration procedures. As the microparticles have a much greater surface area than the same amount of gel not formulated into droplets, their release can be much more precisely controlled and tailored to the specific desired usage. In addition, mass transfer of oxygen and nutrients is more efficient leading to improved cell viability.

According to a first aspect of the present invention, there is provided a method of generating particles comprising decellularized omentum comprising:

(a) dispersing a composition comprising solubilized decellularized omentum in an oil under conditions that allow generation of emulsified, decellularized omentum; and (b) heating the emulsified, decellularized omentum to generate solid particles of decellularized omentum, thereby generating particles comprising decellularized omentum.

As used herein the phrase "decellularized omentum" refers to the extracellular matrix which supports omentum tissue organization which has undergone a decellularization process (i.e., a removal of all cells from the tissue) and is thus devoid of cellular components.

The decellularized omentum comprises extracellular matrix (ECM) components.

The phrase "extracellular matrix (ECM)" as used herein, refers to a complex network of materials produced and secreted by the cells of the tissue into the surrounding extracellular space and/or medium and which typically together with the cells of the tissue impart the tissue its mechanical and structural properties. Generally, the ECM includes fibrous elements (particularly collagen, elastin, and/or reticulin), cell adhesion polypeptides (e.g., fibronectin, laminin and/or adhesive glycoproteins), and space-filling molecules [usually glycosaminoglycans (GAG), proteoglycans].

Omentum may be harvested from mammalian species, such as human, swine, bovine, goat and the like. Following tissue harvesting, the tissue can be either placed in 0.9% saline for immediate processing or stored for later use, preferably at a temperature of about −20° C. to about 80° C.

According to a preferred embodiment, the omentum is derived from a human.

Methods of decellularizing omentum may be found in U.S. Patent No. 20150202348 and WO2014/037942, the contents of which are incorporated herein by reference.

According to one embodiment of the present invention, the decellularization is carried out by:

(a) exposing the omentum to a hypotonic solution;

(b) dehydrating the omentum following step (a);

(c) extracting fat from the dehydrated omentum using polar and non-polar extraction agents following step (b);

(d) rehydrating the dehydrated omentum following step (c); and (e) extracting cells from the rehydrated omentum following step (d).

Omentum may be harvested from mammalian species, such as human, swine, bovine, goat and the like. Following tissue harvesting, the tissue can be either placed in 0.9% saline for immediate processing or stored for later use, preferably at a temperature of about −20° C. to about 80° C.

According to a preferred embodiment, the omentum is derived from a human.

A hypotonic solution is one in which the concentration of electrolyte is below that in cells. In this situation osmotic pressure leads to the migration of water into the cells, in an attempt to equalize the electrolyte concentration inside and outside the cell walls.

Preferably, the hypotonic buffer used by the method according to this aspect of the present invention is 10 mM Tris solution at a pH of about 8.0 and includes approximately 0.1% (w/v) EDTA (5 mM EDTA).

The hypotonic buffer may comprise additional agents such as serine protease inhibitors (e.g. phenylmethanesulfonylfluoride or phenylmethylsulfonyl fluoride, PMSF) and/or anionic detergents such as sodium dodecyl sulphate (SDS).

According to this aspect of the present invention, the tissue is subjected to the hypotonic buffer for a time period leading to the biological effect, i.e., cell swelling and rupture.

Following hypotonic shock, the tissue may optionally be subjected to cycles of freeze-thawing.

The freeze/thaw process preferably comprises freezing the tissue at, for example between −10 to −80° C., and typically at −80° C. for between 2-24 hours and subsequently defrosting the tissue for about 2, 3 or 4 hours until it reaches room temperature or above (for example at 37° C.). This process is carried out at least once and preferably twice or three times in the presence of a hypotonic buffer.

Dehydration involves treating the omentum with one or more dehydration solvents, such one or more treatments of the omentum with a dehydration solvent(s) and/or such solvent(s) in solution with water. The one or more treatments may be sequential steps in the method performed with solutions having different ratios of dehydration solvent(s) to water, such as having gradually reduced amounts of water in the solution for each successive treatment and the final treatment may involve the use of pure solvent, i.e., solvent not in solution with water.

Low molecular weight organic solvents may be used for the dehydration solvent. In an embodiment, the dehydration solvent is one or more alcohols, such as those selected from the group consisting of methanol, ethanol, isopropanol, propanol and combinations thereof.

According to a particular embodiment, the omentum is dehydrated by rinsing once with 70% ethanol (for example for 10-60 minutes) and two to three times in 100% ethanol for 10-60 minutes each.

After dehydration, the fat may be extracted from the omentum using at least one polar solvent and one non-polar solvent, which may occur in one or more extraction steps.

Examples of non-polar solvents are non-polar organic solvents such as hexane, xylene, benzene, toluene, ethyl acetate and combinations thereof. Polar solvents useful for the extraction solvent include acetone, dioxane, acetonithle and combinations thereof. In an embodiment, the extraction solvent is selected from acetone, hexane, xylene and combinations thereof. Nonpolar solvents, include for example hexane, xylene and combinations thereof.

Fat extraction may be conducted in fat extraction steps by contacting the dehydrated omentum with the extraction solvents for varying periods of time.

Preferably, the polar lipids of the tissue are extracted by washing in the polar extraction agent (e.g. 100% acetone) between 10 minutes to 60 minutes. This may be repeated a number of times (e.g. three times). Then, the nonpolar lipids may be extracted by incubating in a mixture of nonpolar: polar agents (e.g. 60/40 (v/v) hexane:acetone solution (with 3 changes) or 60/40 (v/v) hexane:isopropanol solution (with 3 changes)) for about 24 hours.

After the fat extraction, the defatted omentum is optionally re-hydrated. The defatted omentum maybe re-hydrated by contacting the defatted omentum with a re-hydration solvent, such as alcohol or a solution of alcohol in water, such as an alcohol solution having from about 60% to about 70% alcohol. Low molecular weight alcohols, such as methanol, ethanol, isopropanol, propanol and combinations thereof may be used.

The defatted omentum is then decellularized. Any decellularization process known to one skilled in the art may be applied to decellularize the defatted omentum. In an embodiment, the defatted omentum may be decellularized by solubilization of the nuclear and cytoplasmic components. For example, the defatted omentum may be immersed in a decellularization buffer, such as one having non-ionic detergent and metal salt dissolved in acid for a period of time, typically at least about 30 minutes. Non-ionic detergents useful in the invention include polysorbates, such as TWEEN 80, ethoxylated alcohols, such as TRITON® X-100, and polyethanols, such as HP 40 and IGEPAL CA -630 and combinations thereof. Metal salts that may be used include magnesium chloride, phosphate, acetate and citrate, and combinations thereof and these metal salts are typically dissolved in Tris-HCL.

According to another embodiment, the defatted omentum may be decellularized by enzymatic proteolytic digestion which digests cellular components within the tissue yet preserves the ECM components (e.g., collagen and elastin) and thus results in a matrix which exhibits the mechanical and structural properties of the original tissue ECM. It will be appreciated that measures should be taken to preserve the ECM components while digesting the cellular components of the tissue. These measures are further described herein below and include, for example, adjusting the concentration of the active ingredient (e.g., trypsin) within the digestion solution as well as the incubation time.

Proteolytic digestion according to this aspect of the present invention can be effected using a variety of proteolytic enzymes. Non-limiting examples of suitable proteolytic enzymes include trypsin and pancreatin which are available from various sources such as from Sigma (St Louis, Mo., USA). According to one preferred embodiment of this aspect of the present invention, proteolytic digestion is effected using trypsin.

Digestion with trypsin is preferably effected at a trypsin concentration ranging from 0.01-0.25% (w/v), more preferably, 0.02-0.2% (w/v), more preferably, 0.05-0.1 (w/v), even more preferably, a trypsin concentration of about 0.05% (w/v). For example, a trypsin solution containing 0.05% trypsin (w/v; Sigma), 0.02% EDTA (w/v) and antibiotics (Penicillin/Streptomycin, 1000 units/ml and 0.1 mg/mL respectively), pH=7.2] may be used to efficiently digest all cellular components of the tissue.

Preferably, while in the digestion solution, the tissue segments are slowly agitated (e.g., at about 150 rpm) to enable complete penetration of the digestion solution to all cells of the tissue.

It should be noted that the concentration of the digestion solution and the incubation time therein depend on the size of tissue segments utilized and those of skilled in the art are capable of adjusting the conditions according to the desired size and type of tis sue.

Preferably, the tissue segments are digested for at least 1 hour and may be effected for up to 24 hours.

Following decellularization, the omentum may optionally be defatted again (e.g. using a combination of polar and non-polar solvents).

The method according to this aspect of the present invention optionally and preferably includes an additional step of removing nucleic acids (as well as residual nucleic acids) from the tissue to thereby obtain a nucleic acid-free tissue. As used herein the phrase "nucleic acid-free tissue" refers to a tissue being more than 99% free of any nucleic acid or fragments thereof as determined using conventional methods (e.g., spectrophotometry, electrophoresis). Such a step utilizes a DNase solution (and optionally also an RNase solution). Suitable nucleases include DNase and/or RNase [Sigma, Bet Haemek Israel, 20 µg/ml in Hank balance salt solution (HBSS)] or combinations of both—e.g. benzonase. High concentration of salts from 0.5M to 3M, such as sodium chloride, can be used also for nucleic acid elimination.

Next, the cellular components are typically removed from the tissue. Removal of the digested components from the tissue can be effected using various wash solutions, such as detergent solutions (e.g., ionic and non ionic detergents such as SDS Triton X -100, Tween-20, Tween-80) which can be obtained from e.g., Sigma (St Louis, Mo., USA) or Biolab (Atarot, Israel, Merck Germany).

Preferably, the detergent solution used by the method according to this aspect of the present invention includes TRITON-X-100 (available from Merck). For efficient removal of all digested cellular components, TRITON-X-100 is provided at a concentration range of 0.05-2.5% (v/v), more preferably, at 0.05-2% (v/v), more preferably at 0.1-2% (v/v), even more preferably at a concentration of 1% (v/v).

Optionally, the detergent solution includes also ammonium hydroxide, which together with the TRITON-X-100, assists in breaking and dissolving cell nuclei, skeletal proteins, and membranes.

Preferably, ammonium hydroxide is provided at a concentration of 0.05-1.5% (v/v), more preferably, at a concentration of 0.05-1% (v/v), even more preferably, at a concentration of 0.1-1% (v/v) (e.g., 0.1%).

The concentrations of TRITON-X-100 and ammonium hydroxide in the detergent solution may vary, depending on the type and size of tissue being treated and those of skills in the art are capable of adjusting such concentration according to the tissue used. Incubation of the tissue (or tissue segments) with the detergent solution can last from a few minutes to hours to even several days, depending on the type and size of tissue and the concentration of the detergent solution used and those of skills in the art are capable of adjusting such incubation periods. Preferably, incubation with the detergent solution is effected for at least 1 hour.

According to one embodiment, 1-4 cycles of incubation with the detergent solution are performed until no foam is observed.

The above described detergent solution is preferably removed by subjecting the matrix to several washes in water or saline (e.g., at least 3 washes), until there is no evidence of detergent solution in the matrix.

Optionally, the decellularized ECM is then sterilized. Sterilization of the decellularized ECM may be effected using methods known in the art. In an embodiment, the decellularized omentum is contacted with a disinfection solution for a sufficiently effective period of time to disinfect the decellularized omentum, such as at least about 0.5 hour, typically about 1 hour to about 12 hours. The decellularized omentum may be fully submerged in the disinfection solution. The disinfection solution may comprise alcohol, or an alcohol in water solution, and may also include acid. The disinfection solution may include one or more of the following ethanol, methanol, isopropanol, propanol, hydrogen peroxide, peracetic acid and combinations thereof. In an embodiment, the disinfection solution has ethanol, such as 70% ethanol solution. Optionally, the decellularized omentum can be washed one or more times with ultrapure water.

Following washing and optional sterilization, the decellularized tissue may then be dehydrated for example by lyophilization.

Other methods contemplated by the present inventors for decellularizing tissue include those described in U.S. Pat. Nos. 4,776,853, 4,801,299 and U.S. Patent Publication No. 20090163990, the contents of each being incorporated herein by reference in their entirety.

The decellularized omentum of this aspect of the present invention typically comprises less than 20% of the cells as compared to the amount of cells in the omentum prior to decellularization, more preferably less than 15% of the cells as compared to the amount of cells in the omentum prior to decellularization, more preferably less than 10% of the cells as compared to the amount of cells in the omentum prior to decellularization, more preferably less than 5% of the cells as compared to the amount of cells in the omentum prior to decellularization, more preferably less than 2% of the cells as compared to the amount of cells in the omentum prior to decellularization.

In one embodiment, the decellularized omentum is devoid of cellular components.

The phrase "devoid of cellular components" as used herein refers to being more than 90%, 91%, 92%, 93%, 94%, 95%, 96%, 97%, 98%, 99%, (e.g., 100%) devoid of the cellular components present in the natural (e.g., native) omentum.

As used herein, the phrase "cellular components" refers to cell membrane components or intracellular components which make up the cell. Examples of cell components include cell structures (e.g., organelles) or molecules comprised in same. Examples of such include, but are not limited to, cell nuclei, nucleic acids, residual nucleic acids (e.g., fragmented nucleic acid sequences), cell membranes and/or residual cell membranes (e.g., fragmented membranes) which are present in cells of the tissue. It will be appreciated that due to the removal of all cellular components from the tissue, such a decellularized matrix cannot induce an immunological response when implanted in a subject.

The decellularized omentum of this aspect of the present invention is essentially devoid of lipids. The present inventors have found that the extent of extraction of lipids from the tissue correlates with the ability to induce cell attachment, maintain cell viability and promote proper assembly of cells into tissues.

The phrase "devoid of lipids" as used herein refers to a composition comprising less than 10%, 9%, 8%, 7%, 6%, 5%, 4%, 3%, 2%, 1% of the lipids present in the natural (e.g., native) omentum.

Solubilization of the decellularized ECM may be effected as described in Freytes et al., Biomaterials 29 (2008) 1630-1637 and U.S. Patent Application No. 20120156250, the contents of which are incorporated herein by reference.

Typically, in order to carry out solubilization of the decellularized omentum it is first dehydrated e.g. lyophilized.

The lyophilized, decellularized omentum may be cut into small pieces, e.g. crumbled, or milled into a powder and then subjected to a second round of proteolytic digestion. The digestion is effected under conditions that allow the proteolytic enzyme to digest and solubilize the ECM. Thus, according to one embodiment, the digestion is carried out in the presence of an acid (e.g. HCL) so as to obtain a pH of about 1-4.

Proteolytic digestion according to this aspect of the present invention can be effected using a variety of proteolytic enzymes. Non-limiting examples of suitable proteolytic enzymes include trypsin, pepsin, collagenase and pancreatin which are available from various sources such as from Sigma (St Louis, Mo., USA) and combinations thereof. Matrix degrading enzymes such as matrix metalloproteinases are also contemplated.

It should be noted that the concentration of the digestion solution and the incubation time therein depend on the type of tissue being treated and the size of tissue segments utilized and those of skilled in the art are capable of adjusting the conditions according to the desired size and type of tissue.

Preferably, the tissue segments are incubated for at least about 20 hours, more preferably, at least about 24 hours. Preferably, the digestion solution is replaced at least once such that the overall incubation time in the digestion solution is at least 40-48 hours.

Once the decellularized ECM is solubilized, the pH of the solution is increased so as to irreversibly inactivate the proteolytic enzyme (e.g. to about pH 7). The decellularized, solubilized omentum may be stored at this stage at temperatures lower than 20° C.—for example 4° C. so that the decellularized ECM remains in solution.

The solubilized, decellularized omentum is capable of forming a gel at a temperature above about 30° C., above about 31° C., above about 32° C., above about 33° C., above about 34° C., above about 35° C., above about 36° C., above about 37° C.

The liquid form of the solubilized, decellularized omentum is then emulsified in oil (water in oil emulsion-W/O) to produce droplets.

In one embodiment, the oil is a fluorinated oil such as a perfluorinated carbon oil such as FC-40, FC-770, FC-70, FC-77, FC-72, FC-43, FC-3283, FC-3284, perfluoro-hexane (PFH), perfluoro-cyclohexane (PFC), perfluoro-decaline (PFD), perfluoro-perhydrophenanthrene (PFPH) and Novec/hydrofluoroether (HFE)-7500/7100/7200/71DA/71DE/71IPA/72DA/72DE.

In another embodiment, the oil is a hydrocarbon oil (e.g. light mineral oil, heavy mineral oil, hexadecane, tetradecane, octadecane, dodecane, Isopar™ Isoparaffinic fluids or vegetable oil).

The dispersed phase may be broken into droplets by any method known in the art including mixing, colloid milling or homogenizing. Surfactants may be added (during or following the dispersing phase) in order to improve the stability of these systems by separating the droplets and maintaining their shape. Examples of surfactants include, for example pico-surf™1, pico-surf™2, span80, monoolein, oleic acid, tween 20/80, synperonic, PEF, C12E8, SDS, n-butanol, ABIL EM90 and phospholipids.

The addition of surfactant reduces the surface tension between oil and water. Therefore, increasing the concentration of surfactant results in smaller oil droplets.

The next step is separation of omentum-gel droplets from the oil phase. In order to do so, the solution may be centrifuged at an appropriate speed for a number of times so as to remove any residual oil solution.

Another possible way to produce the particles using water in oil strategy is microfluidic fabrication. This approach allows droplet dimensions to be controlled in a very precise manner by adjusting gel and oil phases velocities and by an accurate designing of gel and oil microfluidics channels for the most optimal and homogenous droplet creation. Microfluidics offer many advantages including small requirements for solvents, reagents and cells, low cost and versatility in design.

An additional way to encapsulate cells/biomolecules is using 3D printing. Inkjet bio-printing is a "noncontact" technique that uses electromagnetic technology to deposit tiny droplets of "ink" onto a substrate. Droplet size can be varied by adjusting pulse frequency and ink viscosity. Major advantages of 3D printing are high reproducibility and precise control of droplet size and dose.

Following generation of the particles, the particle is heated so that it hardens. Preferably the particle is heated to a temperature between 30-40° C., for example 34-39° C., for example about 37° C.

The solid particles are then removed from the oil by rinsing them using a hydrophilic solution. In one embodiment, the particles are pipetted with aqueous/hydrophilic solution and then centrifuged, and. The oil solution may then be discarded in order to suspend the particles again in an aqueous/hydrophilic solution. The particles can be transferred to aqueous solution with or without addition of perfluoro-1-octanol (PFO, Sigma-aldrich, Rehovot, Israel).

In one embodiment, the particle is then crosslinked.

Chemical crosslinkers such as Carbodiimides (EDC and DCC), N-Hydroxysuccinimide Esters (NHS Esters), Imidoesters, Maleimides, Haloacetyls, Pyridyl Disulfides, Hydrazides, Alkoxyamines, Aryl Azides, Diazirines, Staudinger Reagent Pairs may be used for crosslinking.

Alternatively, or additionally, enzymes such as transglutaminase, sortase, laccase/peroxidase, lysyl oxidase/amine oxidase may be used. Other enzymes are disclosed in Heck et al., Appl Microbiol Biotechnol. 2013 January; 97(2): 461-475, the contents of which are incorporated by reference.

Chemical crosslinkers that may be used for the present invention include Carbodiimides (EDC and DCC), N-Hydroxysuccinimide Esters (NHS Esters), Imidoesters, Maleimides, Haloacetyls, Pyridyl Disulfides, Hydrazides, Alkoxyamines, Aryl Azides, Diazirines, Staudinger Reagent.

According to another embodiment, the particles are sonicated either prior to or following the cros slinking step.

The generated particles are typically distinct spheres being of a homogeneous size. They form a regular shape such that they are capable of being injected without sticking to one another in a syringe.

Thus, according to another aspect of the present invention there is provided a spherical particle comprising decellularized omentum being between 1 nm-300 µM in diameter.

In one embodiment, the particle is a microparticle (e.g. between 1-300 µm, 30-300 µM, 40-300 µM, 50-300 µM or 100-300 µM).

In another embodiment, the particle is a nanoparticle (e.g. 1-1000 nm, 10-1000 nm or 100-1000 nm).

According to particular embodiments, more than 10%, 20%, 30%, 40%, 50% of the particle is composed of decellularized omentum.

Therapeutic compounds or agents that modify cellular activity can also be incorporated (e.g. encapsulated in, attached to, coated on, embedded or impregnated) into the particles.

For therapeutic agent incorporation, the agents are added to the solubilized decellularized ECM of the omentum.

Exemplary agents that may be comprised into the particles of the present invention include, but are not limited to those that promote cell adhesion (e.g. fibronectin, integrins), cell colonization, cell proliferation, cell differentiation, cell extravasation and/or cell migration. Thus, for example, the agent may be an amino acid, a small molecule chemical, a peptide, a polypeptide, a protein, a DNA, a RNA, a lipid and/or a proteoglycan. Proteins that may be incorporated into the particles of the present invention include, but are not limited to extracellular matrix proteins, cell adhesion proteins, growth factors, cytokines, hormones, proteases and protease substrates. Thus, exemplary proteins include vascular endothelial-derived growth factor (VEGF), activin-A, retinoic acid, epidermal growth factor, bone morphogenetic protein, TGFβ, hepatocyte growth factor, platelet-derived growth factor, TGFα, IGF-I and II, hematopoietic growth factors, heparin binding growth factor, peptide growth factors, erythropoietin, interleukins, tumor necrosis factors, interferons, colony stimulating factors, basic and acidic fibroblast growth factors, nerve growth factor (NGF) or muscle morphogenic factor (MMP). The particular growth factor employed should be appropriate to the desired cell activity. The regulatory effects of a large family of growth factors are well known to those skilled in the art.

As well as, or instead of, the therapeutic compounds of agents described herein above, the present invention further contemplates incorporating (e.g. encapsulating) cells into the particles described herein.

For cell incorporation, the cells are added to the solubilized decellularized ECM of the omentum.

The cells may be derived from any organism including for example mammalian cells, (e.g. human), plant cells, algae cells, fungal cells (e.g. yeast cells), prokaryotic cells (e.g. bacterial cells).

Exemplary cells include cardiac cells, neuronal cells, pancreatic cells, stem cells, liver cells, and muscle cells.

According to a particular embodiment the cells comprise stem cells—e.g. adult stem cells such as mesenchymal stem cells or pluripotent stem cells such as embryonic stem cells or induced pluripotent stem cells. The stem cells may be modified so as to undergo ex vivo differentiation.

According to another embodiment, the cells have been differentiated ex vivo from induced pluripotent stem cells which have themselves been generated from omentum cells.

According to a particular embodiment, the cells are preferably intact (i.e. whole), and preferably viable, although it will be appreciated that pre-treatment of cells, such as generation of cell extracts or non-intact cells are also contemplated by the present invention.

The cells may be fresh, frozen or preserved in any other way known in the art (e.g. cryopreserved).

In one embodiment, the cells are cardiac cells (e.g. human cardiomyocytes). As used herein, the term "cardiomyocytes" refers to fully or at least partially differentiated cardiomyocytes. Thus, cardiomyocytes may be derived from cardiac tissue or from stem cells (such as embryonic stem cells or adult stem cells, such as mesenchymal stem cells). Methods of differentiating stem cells along a cardiac lineage are well known in the art—[Muller-Ehmsen J, et al., Circulation. 2002; 105:1720-6; Zhang M, et al., J Mol Cell Cardiol. 2001; 33:907-21, Xu et al., Circ Res. 2002; 91:501-508, and U.S. Pat. Appl. No. 20050037489, the contents of which are incorporated by reference herein]. According to one embodiment, the stem cells are derived from human stem cell lines, such as H9.2 (Amit, M. et al., 2000. Dev Biol. 227:271).

According to one embodiment, the cardiomyocytes of the present invention are at least capable of spontaneous contraction. According to another embodiment, the cardiomyocytes of the present invention express at least one marker (more preferably at least two markers and even more preferably at least three markers) of early-immature cardiomyocytes (e.g. atrial natriuretic factor (ANF), Nkx2.5, MEF2C and α-skeletal actin). According to another embodiment, the cardiomyocytes of the present invention express at least one marker (more preferably at least two markers and even more preferably at least three markers) of fully differentiated cardiomyocytes (e.g. MLC-2V, α-MHC, α-cardiac actin and Troponin I).

Screening of partially differentiated cardiomyocytes may be performed by a method enabling detection of at least one characteristic associated with a cardiac phenotype, as described herein below, for example via detection of cardiac specific mechanical contraction, detection of cardiac specific structures, detection of cardiac specific proteins, detection of cardiac specific RNAs, detection of cardiac specific electrical activity, and detection of cardiac specific changes in the intracellular concentration of a physiological ion.

In any of the compositions described herein, the decellularized omentum may be derived from the patient himself (i.e. autologous to the patient) or derived from a subject other than the patient (i.e. non-autologous) and/or the cell populations which are administered to the patient together with the decellularized omentum are derived from the patient himself (i.e. autologous to the patient) or derived from a subject other than the patient (i.e. non-autologous).

The particles of the present invention may be used for treating any disorder associated with tissue degeneration. According to a specific embodiment, the compositions are used for treating a cardiac disorder which is associated with a defective or absent myocardium.

Thus, according to another aspect of the present invention there is provided a method of treating cardiac disorder associated with a defective or absent myocardium in a subject, the method comprising transplanting a therapeutically effective amount of the particles of the present invention into the subject, thereby treating the cardiac disorder.

Preferably, the particles of this aspect of the present invention comprise (e.g. encapsulate) cardiac cells. The method may be applied to repair cardiac tissue in a human subject having a cardiac disorder so as to thereby treat the disorder. The method can also be applied to repair cardiac tissue susceptible to be associated with future onset or development of a cardiac disorder so as to thereby inhibit such onset or development.

The present invention can be advantageously used to treat disorders associated with, for example, necrotic, apoptotic, damaged, dysfunctional or morphologically abnormal myocardium. Such disorders include, but are not limited to, ischemic heart disease, cardiac infarction, rheumatic heart disease, endocarditis, autoimmune cardiac disease, valvular heart disease, congenital heart disorders, cardiac rhythm disorders, impaired myocardial conductivity and cardiac insufficiency. Since the majority of cardiac diseases involve necrotic, apoptotic, damaged, dysfunctional or morphologically abnormal myocardium, and since the vascularized cardiac tissue of the present invention displays a highly differentiated, highly functional, and proliferating cardiomyocytic phenotype, the method of repairing cardiac tissue of the present invention can be used to treat the majority of instances of cardiac disorders.

According to one embodiment, the method according to this aspect of the present invention can be advantageously used to efficiently reverse, inhibit or prevent cardiac damage caused by ischemia resulting from myocardial infarction.

According to another embodiment, the method according to this aspect of the present invention can be used to treat cardiac disorders characterized by abnormal cardiac rhythm, such as, for example, cardiac arrhythmia.

As used herein the phrase "cardiac arrhythmia" refers to any variation from the normal rhythm of the heart beat, including, but not limited to, sinus arrhythmia, premature heat, heart block, atrial fibrillation, atrial flutter, pulsus alternans and paroxysmal tachycardia.

According to another embodiment, the method according to this aspect of the present invention can be used to treat impaired cardiac function resulting from tissue loss or dysfunction that occur at critical sites in the electrical conduction system of the heart, that may lead to inefficient rhythm initiation or impulse conduction resulting in abnormalities in heart rate.

The method according to this aspect of the present invention is effected by transplanting a therapeutically effective amount of the particles of the present invention to the heart of the subject (either together with the cardiac cells or without the cardiac cells).

As used herein, "transplanting" refers to providing the particles of the present invention, using any suitable route.

As used herein, a therapeutically effective dose is an amount sufficient to effect a beneficial or desired clinical result, which dose could be administered in one or more administrations. According to one embodiment, a single administration is employed. The injection can be administered into any site in which tissue regeneration is required. For example, for treatment of cardiac disorders, the particles can be administered into various regions of the heart, depending on the type of cardiac tissue repair required. Intramyocardial administration is particularly advantageous for repairing cardiac tissue in a subject having a cardiac disorder characterized by cardiac arrhythmia, impaired, cardiac conducting tissue or myocardial ischemia.

Such transplantation directly into cardiac tissue ensures that the administered cells/tissues will not be lost due to the contracting movements of the heart.

The particles of the present invention can be transplanted via transendocardial or transepicardial injection, depending on the type of cardiac tissue repair being effected, and the physiological context in which the cardiac repair is effected. This allows the administered cells or tissues to penetrate the protective layers surrounding the membrane of the myocardium.

Preferably, a catheter-based approach is used to deliver a transendocardial injection. The use of a catheter precludes more invasive methods of delivery wherein the opening of the chest cavity would be necessitated.

The particles of the present invention can be utilized to regulate the contraction rate of a heart in response to physiological or metabolic state of the recipient individual, thereby serving as a biological pacemaker.

In the case of repairing cardiac tissue in a subject having a cardiac disorder characterized by cardiac arrhythmia, electrophysiological mapping of the heart and/or inactivation of cardiac tissue by radiofrequency treatment may be advantageously performed in combination with administration of the cells and tissues of the present invention if needed.

To repair cardiac tissue damaged by ischemia, for example due to a cardiac infarct, the particles of the present invention is preferably administered to the border area of the infarct. As one skilled in the art would be aware, the infarcted area is grossly visible, allowing such specific localization of application of therapeutic cells to be possible. The precise determination of an effective dose in this particular case may depend, for example, on the size of an infarct, and the time elapsed following onset of myocardial ischemia.

According to one embodiment, transplantation of the compositions of the present invention for repair of damaged myocardium is effected following sufficient reduction of inflammation of affected cardiac tissues and prior to formation of excessive scar tissue.

The present invention can be used to generate cardiomyocytic cells and tissues displaying a desired proliferative capacity, thus cells and tissues are preferably selected displaying a suitable proliferative capacity for administration, depending on the type of cardiac tissue repair being effected. Administration of highly proliferative cells may be particularly advantageous for reversing myocardial damage resulting from ischemia since, as previously described, it is the essential inability of normal adult cardiomyocytes to proliferate which causes the irreversibility of ischemia induced myocardial damage.

Since porcine models are widely considered to be excellent models for human therapeutic protocols and since such models have been widely employed and characterized, it is well within the grasp of the ordinarily skilled artisan to determine a therapeutically effective dose for a human based on the guidance provided herein, and on that provided by the extensive literature of the art.

Determination of an effective dose is typically effected based on factors individual to each subject, including, for example, weight, age, physiological status, medical history, and parameters related to the cardiac disorder, such as, for example, infarct size and elapsed time following onset of ischemia. One skilled in the art, specifically a cardiologist, would be able to determine the amount and number of cells comprised in the composition of the present invention that would constitute an effective dose, and the optimal mode of administration thereof without undue experimentation.

It will be recognized by the skilled practitioner that when administering non-syngeneic cells or tissues to a subject, there is routinely immune rejection of such cells or tissues by the subject. Thus, the method of the present invention may also comprise treating the subject with an immunosuppressive regimen, preferably prior to such administration, so as to inhibit such rejection. Immunosuppressive protocols for inhibiting allogeneic graft rejection, for example via administration of cyclosporin A, immunosuppressive antibodies, and the like are widespread and standard practice in the clinic.

In any of the methods described herein, the particles can be administered either per se or, as a part of a pharmaceutical composition that further comprises a pharmaceutically acceptable carrier.

As used herein a "pharmaceutical composition" refers to a preparation of one or more of the chemical conjugates described herein, with other chemical components such as pharmaceutically suitable carriers and excipients. The purpose of a pharmaceutical composition is to facilitate administration of the particles to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the present invention, the pharmaceutical carrier is an aqueous solution of saline.

Techniques for formulation and administration of drugs may be found in "Remington's Pharmaceutical Sciences," Mack Publishing Co., Easton, Pa., latest edition, which is incorporated herein by reference.

One may administer the pharmaceutical composition in a systemic manner (as detailed hereinabove). Alternatively, one may administer the pharmaceutical composition locally, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

Depending on the medical condition, the subject may be administered with additional chemical drugs (e.g., immunomodulatory, chemotherapy etc.) or cells.

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF. alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A Laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Device design: Microfluidic devices were fabricated by soft lithography. Negative photo resist SU-8 (3050, MicroChem, Corp. Newton, Mass.) was spin-coated onto a clean silicon wafer (300 μm thick, University Wafer, Boston, Mass.) to a thickness of 50 μm and patterned by UV exposure through a transparency photomask. After developing the microstructure, a degassed 10:1 mixture of Sylgard 184 poly(dimethylsiloxane) (PDMS) (Sylgard 184, Dow Corning Corp. Midland, Mich.) and cross-linker (ratio 10:1) was poured onto the pattern, degassed and cured for 1 hour at 65° C. The PDMS molds were peeled off the master and the channel inlets and outlets were made by using a 0.75 mm diameter biopsy punch (World Precision Instruments, Sarasota, Fla.). The PDMS replicas were bonded to a glass slide after oxygen-plasma activation of both surfaces using oxygen plasma (Diener Electronic GmbH & Co. KG, Germany). To avoid wetting of the channels by the dispersed phase, the devices were treated with Aquapel (PPG Industries, Pittsburgh, Pa., USA) by flushing the channels with the solution as received and air dried immediately.

Decellularization of the omentum: Omenta of healthy pigs were purchased from the institute of animal research in Kibutz Lahav, Israel. The fresh tissues were washed with phosphate buffered saline (PBS) in order to deplete blood and debris. Then, the omentum was agitated for 1 hour in a hypotonic buffer of 10 mM Tris 5 mM Ethylenediaminetetraacetic acid (EDTA) and 1 μM phenylmethanesulfonylfluoride (PMSF) at pH 8.0. Next, the tissue went through three cycles of freezing (−80° C.) and thawing (37° C.) using the same buffer. After the last thawing, the tissue was dehydrated by washing it once with 70% ethanol for 30 minutes and three times in 100% ethanol for 30 minutes each. Then the polar lipids of the tissue were extracted by three 30 min washes of 100% acetone. Finely the apolar lipids were extracted by 24 hour incubation in a 60/40 (v/v) hexane:acetone solution (with 3 changes). The defatted tissue was rehydrated by one 30 minute wash in 100% ethanol and an overnight incubation in 70% ethanol at 4° C. Then the tissue was washed four times with PBS at pH 7.4 and was incubated in 0.25% Trypsin-EDTA (Biological Industries, Kibbutz Beit-Haemek, Israel) solution overnight. The tissue was then washed thoroughly with PBS and incubated with 1.5 M NaCl for 24 hours (3 changes) for nucleic acid degradation. Finally the tissue was washed with 50 mM Tris 1% triton-X100 solution at pH 8.0 for 1 hour. The decellularized tissue was washed three times with PBS and three times with double distilled water. The decellularized tissue was frozen (−20° C.) and lyophilized.

Preparation of solubilized omentum dECM: After lyophilization, the decellularized omentum was ground into a coarse powder using a Wiley Mini-Mill and then frozen until further use. Dry, milled omentum dECM was enzymatically digested by adding a 1 mg ml$^{-1}$ solution of pepsin (Sigma, 3200-4500 units mg$^{-1}$ protein) in 0.1 M HCl. The final concentration of dECM was 1% (w/v). The dECM was digested for 96 h at RT under constant stirring until the liquid was homogenous with no visible particles. Subsequently, the pH was raised to 6.5 using 5 M NaOH, then DMEM/F12 (HAM) X10 (Biological industries, Beit-Haemek, Israel) was added and the pH was raised again to 7.2-7.4. Raising the pH terminates pepsin activity (the enzyme is deactivated above pH 6).

Rheological properties: Rheological experiments were performed using a Discovery HR-3 hybrid Rheometer (TA Instruments, DE) with 8 mm diameter parallel plate geometry with a Peltier plate to maintain the sample temperature.

The samples were loaded into the rheometer with the Peltier plate maintaining a temperature of 4° C. The sample was protected from evaporation by wetting of the chamber cover. The temperature was then set to 37° C. to induce gelation; during this time the oscillatory moduli of the sample were monitored continuously at a fixed frequency of 0.127 Hz and a strain of 1%.

Droplet generation: To fabricate omentum-hydrogel droplets, the liquid omentum-hydrogel mixture was loaded into 1 ml sterile disposable syringe (pic solution, Italy). A mixture of 2% Pico-Surf 2 surfactant in perfluorinated carbon oil (Sphere fluidics, Cambridge, United kingdom) was used as the outer phase. Fine Bore Polythene tubings (Smiths Medical International Ltd., Kent, UK) with an outer diameter of 1.09 mm and an inner diameter of 0.38 mm was used to connect the channel inlets with the syringes. Flow rates were controlled by NE-1000 programmable single syringe pump (New era pump systems, USA).

Droplet generation was monitored with a digital microscope (Dino-lite digital microscope, New Taipei city, Taiwan). The flow rates were individually adjusted to obtain the aspired droplet size. Generated droplets were collected from the outlet channel and transferred immediately to 37° C. for four minutes, for their gelation. After gelation, the droplets were transferred into aqueous medium by simple suspension of the droplets.

Following a three minute centrifugation at 600 RPM, the oil phase was discarded and the droplets were re-suspended in culture medium.

Cell culture-3T3 fibroblasts: 3T3 fibroblasts cells were grown in Dulbecco' s Modified Eagle Medium (DMEM) supplemented with 10% (v/v) fetal bovine serum (FBS, Biological Industries, Beit-Haemek, Israel) and 1% (v/v) Penicillin/Streptomycin. The cells were split every five days under sterile conditions and incubated at 37° C. and 5% $CO_2$.

Cardiomyocyte isolation: The left ventricles of 0-3 d-old neonatal Sprague-Dawley rats were harvested and the cells were isolated using 6 cycles (30 min each) of enzyme digestion with collagenase type II (345 U/mg dW, Worthington biochemical corporation, NJ, USA) and pancreatin from porcine pancreas (Sigma-Aldrich, Rehovot, Israel) in DMEM. After each round of digestion, cells were centrifuged (600 g, 5 min) and re-suspended in culture medium composed of M-199 (Biological Industries, Beit-Haemek, Israel) supplemented with 0.6 mM $CuSO_4 \cdot 5H_2O$, 0.5 mM $ZnSO_4 \cdot 7H_2O$, 1.5 mM vitamin B12, 500 U $mL^{-1}$ penicillin and 100 mg $mL^{-1}$ streptomycin, and 0.5% (v/v) fetal bovine serum (FBS). To enrich the cardiomyocyte population, cells were suspended in culture medium with 5% FBS and pre-plated twice for 50 minutes.

Spinal cord motor neurons: Spinal cord motor neurons were differentiated from omentum-derived hiPSCs.

Encapsulation: Prior to encapsulation, cells were counted, centrifuged and resuspended in culture medium to gain the desired cell density and suspended in 9:1 omentum-hydrogel:culture medium mix. The hydrogel mixture was then loaded into a plastic 1 ml syringe for droplet generation as described above. Following gelation, the microgels were transferred into aqueous followed by centrifugation (600 rpm, 3 minutes). The resulting oil phase was discarded and the droplets were re-suspended in cell culture medium. Cell-laden droplets were incubated at 37° C. under 5% $CO_2$. FDA/PI was used to determine the cell viability.

Scanning electron microscopy: For scanning electron microscope (SEM) imaging, samples of cell-laden droplets were fixed with 2.5% glutaraldehyde in PBS for 24 hours at 4° C., followed by dehydration using a graded series of ethanol-water solutions (50-100%). All samples were critical point dried, sputter-coated with gold in a Polaron E 5100 coating apparatus (Quorum technologies, Laughton, UK) and observed under JSM-840A SEM (JEOL, Tokyo, Japan).

Results

Device design: Flow-focusing microfluidics device was designed to encapsulate omentum-gel droplets ca. 50-300 µm in diameter with or without cells. The device has two inlets of surfactant/oil combination (continuous phase) and omentum-hydrogel (dispersed phase), respectively, and one outlet in order to collect the produced droplets (FIG. 1).

Bright Field (BF) microscopy images of the device were taken during the encapsulation process of 3T3 fibroblasts (a model cell line). As can be seen in FIG. 2A, droplets were pinched-off, by the two oil streams, in the droplet production zone. Droplets were stabilized by the surfactant while flowing to the outlet stream of the device (FIG. 2B).

Omentum-hydrogel rheological measurements: Rheological properties of the omentum-hydrogel is important characteristics in order to predict its behavior under applied forces. When the temperature was elevated from 4 to 37° C. and during the gelation period, both the storage modulus (G') and the loss modulus (G") increased over time, and were characterized by a sigmoidal shape (FIG. 3). As G' was greater than G" throughout the measurements, the omentum-hydrogel possess pronounced elastic gel properties, which is essential for cardiac engineered tissue.

Optimization of pico-surf™2 surfactant in FC-40 oil for maintaining cell viability: Different percentages of pico-surf™ 2 surfactant were tested. The viability of encapsulated 3T3 fibroblasts cells was investigated in order to prove that the encapsulation process is not toxic to the cells. As can be seen in FIG. 4A, high viability percentages were achieved for both surfactant concentrations. In addition, droplet diameter was measured for each experiment to examine the size distribution of the encapsulation process. As can be seen in FIGS. 4B and 4C, droplet diameter mean size, using 5% and 2% pico-surf™2, was 73.71 µm and 67.86 µm, respectively. The droplet mean size was reproducible using 5% and 2% surfactant and Gaussian size distribution was achieved for both. Using 5% surfactant, a wider distribution can be seen (FIG. 4B), which may be attributed to chunks of omentum-hydrogel plugging the channel of the dispersed phase, leading to changes in the dispersed phase velocity which resulting in disrupted flow profile in the nozzle zone. Since there were no significant differences between the 5% and 2% surfactant, 2% pico-surf™2 was chosen for further experiments.

Dispersed phase velocity effect on droplet production and cell viability: Through changing continuous and dispersed phase velocities, the droplet size can be controlled. Thus, dispersed phase velocities were changed and cell viability and droplet diameter were examined. As can be seen in FIG. 5A, viability of encapsulated 3T3 fibroblasts cells was excellent for each of the velocities. Mean droplet diameter using 20, 40 and 60 µl $hr^{-1}$ dispersed phase velocity, were 64.01, 67.86 and 79.42 µm, respectively (FIG. 5B). As expected, as the dispersed phase velocity was increased, the droplet diameter increased as well. Using a velocity of 20 µl $hr^{-1}$ (FIG. 5C), a narrow Gaussian distribution was achieved. Higher velocities (40 and 60 µl $hr^{-1}$, FIGS. 5D and 5E, respectively) resulted in wider Gaussian distribution, reaching 150 µm size droplets.

As can be seen in FIG. 6A, significant amount of homogenous droplets was produced while a high percentage contained encapsulated cells. The surfactant preventing coalescence of the droplets, resulting in stable, well ordered droplets. After separation of droplets into an aqueous medium, live/dead assay was conducted, for the quantification of cell viability. FIG. 6B is a visual example for the high cell viability that was achieved using the present system.

Continuous phase velocity effect on droplet production and cell viability: Continuous phase velocity was changed and cell viability and droplet diameter were examined. As can be seen in FIG. 7A, viability of encapsulated 3T3 fibroblasts cells was excellent irrespective of the continuous phase velocity. Mean droplet, using 60, 80 and 100 μl hr$^{-1}$ continuous phase velocity, was 77.6, 74.2 and 73.2 μm, respectively (FIG. 7B). There was a good correlation between continuous phase velocity and droplet diameter. As continuous phase velocity increased, so droplet diameter decreased. Using a velocity of 60 μl hr$^{-1}$ (FIG. 7C), a wide Gaussian distribution was reached. The oil velocity is too low in order to pinch the droplets homogenously. Higher velocities (80 and 100 μl hr$^{-1}$, FIGS. 7D and 7E, respectively) resulted in narrower Gaussian distribution, reaching 65% of droplets in diameter of 70-75 μm. The effect of increasing continuous phase velocity was not dominant as increasing dispersed phase velocity, as expected. It is attributed to the higher viscosity of the omentum-hydrogel compared to the oil phase viscosity.

Cell concentration effect on droplet production and cell viability: Cell concentration was changed and cell viability and droplet diameter were examined. As can be seen in FIG. 8A, viability of encapsulated 3T3 fibroblasts cells was not affected by cell concentration. Using 25×10$^6$ and 50×10$^6$ cells mL$^{-1}$, the number of cells per droplet was 4.4 and 17, respectively (FIG. 8B). Using 25×10$^6$ and 50×10$^6$ cells mL$^{-1}$, a narrow Gaussian distribution was achieved (FIG. 8C and 8D, respectively).

SEM images of omentum-hydrogel droplets: In order to confirm omentum fiber existence and its support to the cells, after droplet production and separation, omentum-hydrogel droplets with and without encapsulated cells were imaged using SEM. As can be seen in FIGS. 9A-B, cells were encapsulated within the omentum-hydrogel in a way that each cell is surrounded by the omentum-fibers, providing mechanical and biochemical support.

Immunofluorescence staining of encapsulated cells in omentum-hydrogel droplets: hiPSCs were differentiated to spinal cord neurons in culture until day 19, then encapsulated within omentum-hydrogel droplets and were cultured whilst being differentiated until day 28. On day 30, droplets were fixed and encapsulated neurons were stained for β-tubulin and nuclei while the omentum-hydrogel droplets were stained for collagen I. The encapsulated cells are illustrated in FIGS. 10A-C.

In addition, neonatal cardiomyocytes (CMs) were isolated and encapsulated within omentum-hydrogel droplets, fixed at day 8 (FIGS. 11A-B) and day 13 (FIGS. 11C-D) and were stained for collagen I, nuclei and actinin. As can be seen in FIGS. 11A-D, all CMs spread evenly within the omentum-hydrogel droplet.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition comprising a plurality of spherical particles being between 50-300 μm in diameter, wherein said spherical particles encapsulate biological cells, wherein said spherical particles consist of decellularized omentum and biological cells.

2. The composition of claim 1, wherein said omentum comprises human omentum.

3. The composition of claim 1, wherein said biological cells are selected from the group consisting of cardiac cells, neuronal cells, pancreatic cells, stem cells, liver cells, muscle cells, blood cells and immune cells.

4. The composition of claim 1, wherein each of the particles of said plurality of particles are of substantially the same size.

5. The composition of claim 1, which does not induce an immunological response when implanted in a subject, when said omentum is autologous to said subject.

6. The composition of claim 1, wherein said biological cells comprise cardiomyocytes.

7. The composition of claim 1, wherein said spherical particles are between 100-300 μm in diameter.

8. The composition of claim 1, being generated by a method comprising:
   (a) dispersing a composition comprising solubilized decellularized omentum and biological cells in a mixture comprising a fluorinated oil and surfactant, under conditions that allow generation of droplets of emulsified, decellularized omentum;
   (b) heating said droplets of emulsified, decellularized omentum to generate solid particles which consist of decellularized omentum and biological cells; and
   (c) separating said solid particles consisting of decellularized omentum from said mixture following said heating, wherein said method is effected using a microfluidics device.

9. A method of treating a disease or medical condition which would benefit from cell transplantation in a subject in need thereof, comprising administering to the subject a therapeutically effective amount of a plurality of the particles of claim 1, thereby treating the medical condition.

* * * * *